(12) United States Patent
Ho et al.

(10) Patent No.: US 8,263,104 B2
(45) Date of Patent: Sep. 11, 2012

(54) POLYMER NANOFILM COATINGS

(75) Inventors: Dean Ho, Chicago, IL (US); Mark Chen, Chicago, IL (US); Erik Pierstorff, Highland Park, IL (US); Houjin Huang, Evanston, IL (US); Edward K Chow, Rancho Palos Verdes, CA (US); Genhong Cheng, Calabasas, CA (US)

(73) Assignees: Northwestern University, Evanston, IL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/135,640

(22) Filed: Jun. 9, 2008

(65) Prior Publication Data

US 2009/0004241 A1    Jan. 1, 2009

Related U.S. Application Data

(60) Provisional application No. 60/942,885, filed on Jun. 8, 2007, provisional application No. 60/981,688, filed on Oct. 22, 2007.

(51) Int. Cl.
*A61F 2/02* (2006.01)
*A61K 31/56* (2006.01)

(52) U.S. Cl. ........................ 424/423; 514/178
(58) Field of Classification Search ............ None
See application file for complete search history.

(56) References Cited

U.S. PATENT DOCUMENTS

| | | | | |
|---|---|---|---|---|
| 6,723,814 | B2 * | 4/2004 | Meier et al. | 526/279 |
| 7,211,108 | B2 * | 5/2007 | Furst et a | 623/1.44 |
| 7,419,709 | B2 * | 9/2008 | Rypacek et al. | 428/36.9 |
| 2003/0228681 | A1 * | 12/2003 | Ritts et al. | 435/287.2 |
| 2004/0142011 | A1 * | 7/2004 | Nilsson et al. | 424/422 |
| 2006/0088571 | A1 * | 4/2006 | Chen et al. | 424/426 |
| 2006/0222756 | A1 * | 10/2006 | Davila et al. | 427/2.24 |
| 2007/0197890 | A1 * | 8/2007 | Boock et al. | 600/365 |
| 2007/0259101 | A1 * | 11/2007 | Kleiner et al. | 427/2.24 |
| 2008/0075753 | A1 * | 3/2008 | Chappa | 424/426 |

OTHER PUBLICATIONS

Ho et al. "Attenuation of Cellular Inflammation Using Glucocorticoid-Functionalized Copolymers" Conference on Nano/Micro Engineered and Molecular Systems Jan. 16-19, 2007.*
Nardin et al. "Giant Free-Standing ABA Triblock Copolymer Membranes" 2000 Lengmuir. 16: 7708-7712.*
Burt et al., "Thug-eluting stents: A multidisciplinary success Story," 2006 Advanced Drug Delivery Reviews, vol. 58, pp. 350-357.
Burt et al., "Drug-eluting stents: an innovative multidisciplinary drug delivery platform," 2006 Advanced Drug Delivery Reviews, vol. 58, pp. 345-0346.
Ghannam et al., "Interaction of type-I collagen with phospholipid monolayer" 1999 Biophys. Chem. 80:31-40.
Graff et al., "Virus-Assisted Loading of Polymeric Nanocontainers" 2002 Proc Nat Acad. Sci. 99:5064-5068.
Grant et al, "Layer-By-Layer Assembly of Collagen Thin Films: Controlled Thickness and Biocompatibility" 2001 Biomed Microde v 3:301•306.
Grattan et al., "The thermal aging of parylene and the effect of antioxidant," 1991 Studies in Conservation, vol. 36, pp. 44-52.
Grube et al, "Six-month clinical and angiograplric results of a dedicated drug-eluting stent for the treatment of coronary bifurcation narrowings," 2007 The American Journal of Cardiology, vol. 99, pp. 1691-1697.
Ho et al., "Fabrication of biofunctional nanomaterials via *Eschericlria coli* OmpF protein air water interface insertion/integration with copolymeric amphiphiles" 2006 Nanomedicine 2: 103-112.
Ho et al., "Fabrication of biomolecule-copolymer hybrid nanovesicles as energy conversion systems" 2005 Nanotechnology 16:3120-3132.
Ho et al., "Functionalizing Biomimetic Membranes with Energy Transducing Proteins" 2004 Proc. of the Mat. Res. Soc. 823:W11.8.1-W11.8.6.
Ho et al., "Hybrid Protein/Polymer Biomimetic Membranes" 2004 IEEE Trans. Nanotechnology. 3:256-263.
Ho et al., "Protein-driven energy transduction across polymeric biomembranes" 2004 Nanotechnology 15:1084-1094.
Krucoff et al., "Drug-eluting stents 'deliver heartburn'—How do we spell relief going forward," 2007 Circulation, vol. 115, pp. 2990-2994.
Lee et al., "Biosolar Powered Fabric" IEEE 2003 Proceedings on Nanotechnology 2:733-736.
Lee et al., "Fluorometric Measurement of Vectorially-Inserted Purple Membrane Activity Across Block Copolymer Thin Films" 2006 Polymer 47:2935-2941.
Luecke et al., "The glucocorticoid receptor blocks P-TEFb recruitment by NFkappaB to effect promoter-specific transcriptional repression" 2005 Genes Dev. 19:1116-1127.
Malafaya et al., "Natural-origin polymers as carriers and scaffolds for biomolecules and cell delivery in tissue engineering application," 2007 Advanced Drug Delivery Reviews, vol. 59, pp. 207-233.
Meier et al., "Reconstitution of Channel Proteins in (polymerized) ABA Tri-block Copolymer Membranes" 2000 Angew Chim Int Ed 39:4599-4602.
Nardin et al., "Giant Free-Standing ABA Triblock Copolymer Membranes" 2000 Langmuir. 16:7708-7712.
Nardin et al., "Polymerized ABA-tri-block copolymer vesicles" 2000 Langmuir 16:1035-1041.
Rathman et al., "Biocomposite films synthesized at a fluid/fluid interface" 2005 Faraday Disc 129: 193-203.

(Continued)

*Primary Examiner* — Robert A Wax
*Assistant Examiner* — Danah Al-Awadi
(74) *Attorney, Agent, or Firm* — Casimir Jones, S.C.

(57) ABSTRACT

Disclosed herein are nanofilm coatings for implantable medical devices comprising a diblock or triblock copolymer (PEO-PMMA or PMOXA-PDMS-PMOXA, respectively). Such nanofilms, may be used, for example, as amphiphilic supports for therapeutic agents. These materials are conducive towards the formation of active substrates for a suite of biological and medical applications.

6 Claims, 19 Drawing Sheets

OTHER PUBLICATIONS

Sokolsky-Papkov et al., "Polymer carriers for drug delivery in tissue engineering," 2007 Advanced Drug Delivery Reviews, vol. 59, pp. 187-206.

Stark, "Literature review: Biological safety of parylene C," 1996 Medical Plastics and Biomaterials, p. 30.

Stoeckenius et al., "Structure of biological membranes" 1979 Biochem. Biophys Acta 505:215-278.

Szucs et al., "Stable and Reversible Electrochemistry of Cytochrome-C on Bare Electrodes .2. Effects of Experimental Conditions" 1995 Journal of Electroanalytical Chemistry, 383:75-84.

Terrettaz et al., "Kinetic Parameters for Cytochromec via Insulated Electrode Voltammetry" 1996 Journal of the American Chemical Society 118:7857-7858.

Wolgemuth, "Assessing the performance and suitability ofpatylene coating," 2000 Medical Device and Diagnostic Industry, p. 42.

Wong et al., "Chemotherapy with anticancer drugs encapsulated in solid lipid nanoparticles," 2007 Advanced Drug Delivery Reviews 59 pages 491-504.

Xi et al., "Lessons Learned From Engineering Biologically-Active Hybrid Nano/Micro-devices" 2005 Advanced Functional Materials 15:1233-1240.

* cited by examiner

A.

B.

A. Control

B. Uncoated

C. PolyDex Coated

POLYMER NANOFILM COATINGS

This application claims priority to U.S. Provisional patent application 60/942,885, filed Jun. 8, 2007, and U.S. Provisional Application 60/981,688, filed Oct. 22, 2007, both of which are herein incorporated by reference in their entireties.

This invention was made with government support under Grant No. A1065359 awarded by NIH. The government has certain rights in the invention.

FIELD OF THE INVENTION

The present invention relates generally to the field of coatings for medical and pharmaceutical applications. In particular, the present invention relates to medical and pharmaceutical products having biocompatible nanofilms comprising therapeutic agents.

BACKGROUND

Implantable medical devices are becoming increasingly common and more complex. Advances in medical device technology have led to smaller and more complex implants that provide a greater standard of living to an increasingly aging population. However, not all of the materials used in medical implants are entirely biocompatible, i.e. the surrounding tissues may become inflamed when in contact with the surface of the implant. Inflammation results from the infiltration of immune cells such as neutrophils and macrophages to the tissue-implant interface as these cells attempt to repair damage that occurs following implantation. Thus, inflammatory responses against implants remains a problem with respect to both tolerance and maintenance of function for a variety of these implants, ranging from cardiovascular devices (e.g. coronary stents) and electrical devices (e.g. pacemakers and glucose sensors to prostheses such as hip joint replacements). Accordingly, there is a need for biocompatible materials which can coat the implant and serve as vehicles for the targeted delivery of drugs to the surrounding tissues.

Existing delivery technologies include the use of poly(lactic-co-glycolic acid) (PLGA) microspheres as drug-eluting particles for suppression of inflammation. The use of fluidic delivery of anti-inflammatories has also been explored. In addition, poly(3,4-ethylenedioxythiophene) (PEDOT) has been used in nanotube and planar formats. Unfortunately, each of the delivery systems provide a relatively thick material associated with an implant. For example, the PLGA microspheres are on the order of 200 microns in diameter, while fluidic delivery materials are several microns in thickness. As a result, these materials significantly impact the design parameters of the implants they serve and generate adverse effects on surrounding tissues because they increase the overall dimensions of the implants and preclude non-invasive behaviors.

In addition, all invasive biomedical devices inherently possess the challenge of overcoming three primary obstacles. These concerns are biocompatibility, bio-longevity, and efficacy. Biomedical devices desire to leap these hurdles and be completely biocompatible to reduce the risk of patient complications, but often, current technologies result in new drawbacks. For example, many types of drug-eluting stents serve to reduce clotting of the stent in implant patients, but are associated with increased clinical complication rates. Because recent advances do not optimally address implant biocompatibility, newer, more effective mechanisms are a necessity.

Pioneering drug delivery as a new field for parylene-based applications fills the need for a biocompatible, functionalized membrane capable of slow-releasing drug to a localized region for targeted delivery. Currently, chemotherapeutic drugs are capable of killing cancerous cells, but cannot selectively kill only cancerous cells; they exhibit universal cytotoxicity. A similar issue exists in administering anti-inflammatory compounds; indiscriminately introducing these compounds significantly dilute drug efficacy and weaken the global immune response, which opens a window for infection. Therefore, it is imperative that drugs are delivered in a targeted fashion.

Drug delivery is an important aspect of medicine as an essential mechanism that bridges drug development and treatment. During the past decade, there has been much attention focused on improving control of drug delivery and the advent of newer technologies including tissue scaffolds and drug-eluting stents is evidence of the desire to have more control over how, where, and when pharmaceutical agents are delivered. Nevertheless, it has been a challenge to create a biocompatible coating capable of eluting drug due to several developmental barriers. Such a material would need to be biologically inert and stable, possess anti-inflammatory mechanisms, and pliable for use in a wide variety of applications. With these criteria in mind, the biomedical industry has sought to create a biocompatible coating that does not interfere with device operation, may abate inflammatory responses, and bolster efficacy of the coated mechanism.

An example of such a search led to the creation of the drug-eluting stent. The drug-eluting stent was created to improve stent longevity and minimize clotting on the stent itself to reduce the risk of neointimal hyperplasia, an excessive immune response to bare metal stent implants that results in narrowing of vessels due to clots, and thus medical complications for the patient. By eluting immunosuppressive drugs from the stent, the inflammatory response was lessened near the implant location of the stent, thus inhibiting platelet activation and preventing neointimal hyperplasia. The drug-eluting stent has revolutionized cardiology, but many stents rely on less than ideal materials, or an unsuitable combination of materials.

For example, while the FDA has concluded that drug-eluting stents are safer and more effective than bare metal stents, certain complications may result from using a drug-eluting stent including severe thrombotic (formation of clot inside a blood vessel) events and restenosis (abnormal narrowing of vessels), despite restenosis and thrombosis being some of the very issues drug eluting stents were created to solve. Therefore, while modern stents are a step forward in reaching complete biocompatibility of implanted devices, much of the present technology is not progressive enough, and the search and necessity for a more biocompatible coating continues.

SUMMARY OF THE INVENTION

The present invention relates generally to the field of coatings for medical and pharmaceutical applications. In particular, the present invention relates to medical and pharmaceutical products having biocompatible nanofilms comprising therapeutic agents.

The present invention relates to nanoscale copolymer thin films associated with therapeutic agents to provide copolymer-therapeutic agent complexes. The invention further relates to the use of the thin films as coatings in medical applications to provide localized therapeutic agent delivery. Polyethleneoxide-polymethylmethacrylate (PEO-PMMA)

diblock copolymers and polymethyloxazoline-polydimethylsiloxane-polymethyloxazoline (PMOXA-PDMS-PMOXA) triblock copolymers are examples of copolymers that may be used in the present thin films. The use of amphiphilic diblock and triblock copolymers in the formation of multifunctional nanofilms for the coating of implants is advantageous because these copolymers facilitate the incorporation of a wide variety of therapeutic agents into the coatings. In certain embodiments, the copolymer materials of the present invention are combined with an anti-inflammatory molecule. The present invention contemplates any type of suitable anti-inflammatory molecule. Such molecules are known in the art and can be easily located in the literature.

In addition to providing a mechanism for localized therapeutic agent delivery, the present coatings, in certain embodiments, facilitate chronic device functionality and prevent, delay or minimize bio-fouling of implanted medical devices, such as implants. In addition, the coatings may also be useful for single-cell studies to examine polymeric activation of cellular gene expression pathways for biotic-abiotic interfacing studies (e.g. mechano-sensation, metabolism, etc.). The copolymer-therapeutic agent complex coatings optionally may be used in conjunction with vesicular therapeutic agent delivery structures to provide replenishment of the therapeutic agents in the coatings. In such an embodiment, copolymers may also be assembled into vesicular structures that can serve as reservoirs for the therapeutic agents. Surface functional groups on these vesicles interact with the copolymer coatings on a medical implant to enable intelligent, localized delivery of the therapeutic agents to specific areas, including thin film coatings that require drug replenishment. In addition, the vesicular structures provide the ability to target and facilitate on-demand vesicular endocytosis to prevent excessive dosing. As such, these materials may serve as a modality for novel medical capabilities, as well as a platform for fundamental cellular studies.

The present copolymer coatings may be produced using Langmuir-Blodgett (LB) deposition. Details regarding the LB deposition process are provided in Example 2, below. Using this method, a self-assembled copolymer-therapeutic agent complex may be fabricated by adding a therapeutic agent (e.g., a hydrophilic agent) atop a pre-deposited copolymer layer on a Langmuir trough. The use of the LB method is advantageous because it allows for the deposition of very thin copolymer films (e.g., ≦5 nm) and provides films with controlled molecular spacing that adsorb in a very robust manner to a variety of underlying substrates. In addition, the method can be used to deposit a spectrum of therapeutic agents with a variety of hydrophilic/hydrophobic properties that resist the generation of clumps or aggregates that may adversely affect cell behavior or the biocompatibility of cells that come into contact with the nanofilm coatings. Furthermore, the LB method allows for a layer-by-layer deposition of copolymer-therapeutic agent complex thin films, making it possible to tune the coating thickness and therapeutic agent concentration to control how much of the therapeutic agent is associated with an implant surface. The present LB methods and the resulting LB nanofilms are easily distinguished from thin films produced by the Langmuir technique which creates a thin film over an opening or aperture, rather than on an underlying substrate.

In certain embodiments, the present invention provides an implantable medical device having one or more of its surfaces coated with a nanofilm composition comprising a copolymer, wherein the copolymer may be, for example, (i) a diblock copolymer comprised of polyethylene oxide-polymethyl methacrylate or (ii) a triblock copolymer comprised of polymethyloxazoline-polydimethylsiloxiane-polymthoxazoline.

In one aspect, the present invention provides an implantable medical device having one or more of its surfaces coated with an nanofilm composition comprising: (a) at least one therapeutic agent (e.g., wherein the therapeutic agent is not a protein); and (b) a copolymer, wherein the copolymer may be, for example, (i) a diblock copolymer comprised of polyethylene oxide-polymethyl methacrylate or (ii) a triblock copolymer comprised of polymethyloxazoline-polydimethylsiloxiane-polymthoxazoline.

The copolymers desirably, but not necessarily, comprise monomer units having acrylate endgroups, which may facilitate crosslinking and film stability. The nanofilm coatings of the present invention may also comprise endgroups attached to a receptor or a ligand, which may facilitate subsequent target delivery of additional therapeutic agents, as described in more detail below. A single layer of the copolymer in a nanofilm may be designed to have a thickness from about 1 nm to about 10 nm (e.g., 1, 2, 3, 4, 5, 6, 7, 8, 9, or 10 nm), desirably less than about 4 nm. However, the nanofilm may include multiple layers (e.g., from about 2 to about 10 layers) of the copolymer-therapeutic agent complexes, wherein each layer has a thickness from about 1 to about 10 nm (e.g., about 4 nm or less).

The therapeutic agent may be selected from the group consisting of, for example: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In one embodiment, the therapeutic agent is an anti-inflammatory compound, e.g. Dexamethasone or an LXR agonist. In particular embodiments, the LXR agonist is 3-((4-Methoxyphenyl)amino)-4-phenyl-1-(phenylmethyl)-1H-pyrrole-2,5-dione. In particular embodiments, the LXR agonist functions as a non-steroidal anti-inflammatory to block transcriptional machinery associated with cell stress among other disorders. In certain embodiments, the therapeutic agent is one or more of the following: sirtuin Activators, cytokines, interferons of all kinds (e.g. alpha, beta, gamma, etc), as well as any other suitable therapeutic molecule.

The nanofilm coatings of the present inventions may be used on a variety of medical substrates, including any implantable medical device. Such medical devices may be made of a variety of biocompatible materials including, but not limited to, polymers and metals. Medical substrates onto which the nanofilms may be coated include, neural/cardiovascular/retinal implants, leads and stents, and dental implants (e.g. nanofilms to seed bone growth). In some embodiments, the nanofilm may be coated onto the electrode of an implantable medical device. In fact, coating the present nanofilms onto an electrode may provide an important medical advantage because the copolymer films prevent or minimize bio-fouling which often begins at the site of a metal electrode. In addition, unlike more conventional implant coatings, the present nanofilms may be made thin enough that they do not interfere with electrode function (e.g., electrical conductivity or redox reactions at electrodes).

In another aspect, the present invention provides a method of delivering a therapeutic agent to a target site in a subject, the method comprising: (1) coating an implantable device with a nanofilm composition comprising: (a) at least one therapeutic agent (e.g., wherein the therapeutic agent is not a protein); and (b) a copolymer, wherein the copolymer may be, for example, (i) a diblock copolymer comprised of polyethylene oxide-polymethyl methacrylate or (ii) a triblock copolymer comprised of polymethyloxazoline-polydimethylsiloxiane-polymthoxazoline; and (2) implanting the device into the subject near the target site, wherein elution of the therapeutic agent from the nanofilm delivers the therapeutic agent to the target site.

This method may further comprise the step of administering to the subject a vesicle, wherein the vesicle comprises (a) at least one additional therapeutic agent, wherein the additional therapeutic agent is the same or a different therapeutic agent as used in the device; and (b) a copolymer, wherein the copolymer may be, for example, (i) a diblock copolymer comprised of polyethylene oxide-polymethyl methacrylate or (ii) a triblock copolymer comprised of polymethyloxazoline-polydimethylsiloxiane-polymthoxazoline; and wherein the copolymer comprises monomer units having endgroups covalently attached to a second receptor or ligand, wherein the second receptor or ligand is capable to specifically binding to a first receptor or ligand attached to endgroups on the nanofilm coating. This additional step allows for the interaction of the vesicle with the nanofilm for the purpose of releasing the additional therapeutic agent into the nanofilm.

In some embodiments, the present invention provides membranes comprising: a) a first layer comprising parylene, and b) a second layer comprising a copolymer selected from the group consisting of polyethylene oxidepolymethylmethacrylate, polymethyloxazoline-polydimethylsiloxiane-polymthoxazoline, and a mixture thereof. In particular embodiments, the membrane comprises a third layer, wherein the third layer comprises parylene. In other embodiments, the second layer is between the first and second layers. In other embodiments, the membranes further comprise at least one therapeutic agent. In further embodiments, the at least one therapeutic agent is within the second layer. In other embodiments, the first layer comprises nonporous parylene. In particular embodiments, the third layer comprises rough parylene C.

In some embodiments, the present invention provides a device comprising an active parylene-encapsulated co-polymeric (APC) membrane for slow release drug delivery. Such devices may be implantable medical devices and comprise a base layer, which may serve as a backbone of the membrane, an upper layer coated with a nanofilm composition, that may act as a semi-permeable membrane; and a copolymeric matrix capable of being conjugated with a molecule, wherein the matrix comprises a network matrix of a copolymer selected from the group consisting of di-block copolymers such as polyethylene oxide-polymethyl methacrylate, tri-block copolymers such as polymethyloxazoline-polydimethylsiloxiane-polymthoxazoline, and mixtures thereof, and a therapeutic agent, wherein the matrix is conjugated with the therapeutic agent. Thus, in some embodiments, a membrane is provided comprising a base layer having a first and a second surface; a copolymeric layer having a first and a second surface and comprising a copolymer selected from the group consisting of polyethylene oxide-polymethyl methacrylate, polymethyloxazoline-polydimethylsiloxiane-polymthoxazoline, and a mixture thereof, a coating having a first and a second surface and comprising a nanoporous, parylene film; and a therapeutic agent; wherein the copolymeric layer is conjugated with the therapeutic agent; the first surface of the base layer is in contact with the second surface of the copolymeric layer and the second surface of the coating is in contact with the first surface of the copolymeric layer, such that a sandwich structure is achieved.

In another aspect, parylene, an FDA approved biologically inert nanomaterial capable of being deposited uniformly on virtually any surface, may be used to prepare an active parylene-encapsulated copolymer (APC) membrane that can be applied to implants, sensors, stents, and a wide array of other invasive biomedical devices. This novel membrane technology can serve as both a coating based modality or a stand-alone device for targeted therapeutic delivery, demonstrating its versatile range of medically-significant functionalities. APC membranes are capable of being functionalized with a diverse selection of compounds for specialized treatment including, but not limited to cancer, inflammation, and anti-viral therapies Furthermore, APC membranes have slow-release capabilities that enhance the bio-longevity of a device by several days, as revealed through RT-PCR gene expression studies. In addition, the slow release mechanism targets drug elution to a localized area near the membrane, thereby augmenting the efficacy of the drug by concentrating the effective dosage to the targeted region and limiting drug that is haphazardly flushed through the patient's entire system. This method of drug delivery offers significant benefits especially for chemotherapy and anti-inflammation therapies that have serious consequences when drugs are arbitrarily carried through the patient's system.

In yet another aspect, an APC membrane is described. Such APC membranes are parylene-based functionalized drug delivery membranes capable of targeted and slow-release drug elution capabilities, and also having the flexibility to be tailored to any surface as well as to many therapeutic applications. The APC membrane fulfills the need for localized delivery through its flexibility and slow-release mechanism by acting as a reservoir for a spectrum of therapeutic compounds. Because the nanopore layer of the APC membrane is capable of trapping the drug and eluting it slowly through the membrane as it comes into contact with fluids, the effective dose of the drug will be applied in a very controlled and precise fashion that contains the drug concentration near the surface of the membrane. This is ideally applicable for the patient because the drug effect is localized and the effective dose is utilized in its entirety. The prime level of specificity and biocompatibility that has been effectively engineered into the APC membrane and will serve as a flexible, functionalized platform capable of creating a controlled window where neither infection nor implant rejection occurs, and localizing drug activity to cancerous regions that will enhance chemotherapy potency and ultimately, benefit the patient's life and well being.

In a related aspect, stable packagings of the tri-block copolymeric nanofilm, are provided, so that device technologies can be developed while using the copolymeric membrane as a foundational drug elution matrix. As parylene is coated on a device through room temperature vapor deposition of individual molecules, the resulting coating is extremely uniform, and conforms to practically any surface shape. This property is important for many biomedical devices that require isolation from the body to preserve the function of the device. Furthermore, the middle layer of the APC membrane is a network matrix of tri-block copolymer that may be conjugated with a very broad spectrum of drug molecules.

BRIEF DESCRIPTION OF THE DRAWINGS

FIG. 14 shows that parylene and the APC membrane have comparable cell adhesion properties; RT-PCR results reveal contrasting levels of inflammatory cytokine expressed.

DETAILED DESCRIPTION

Figure 1:
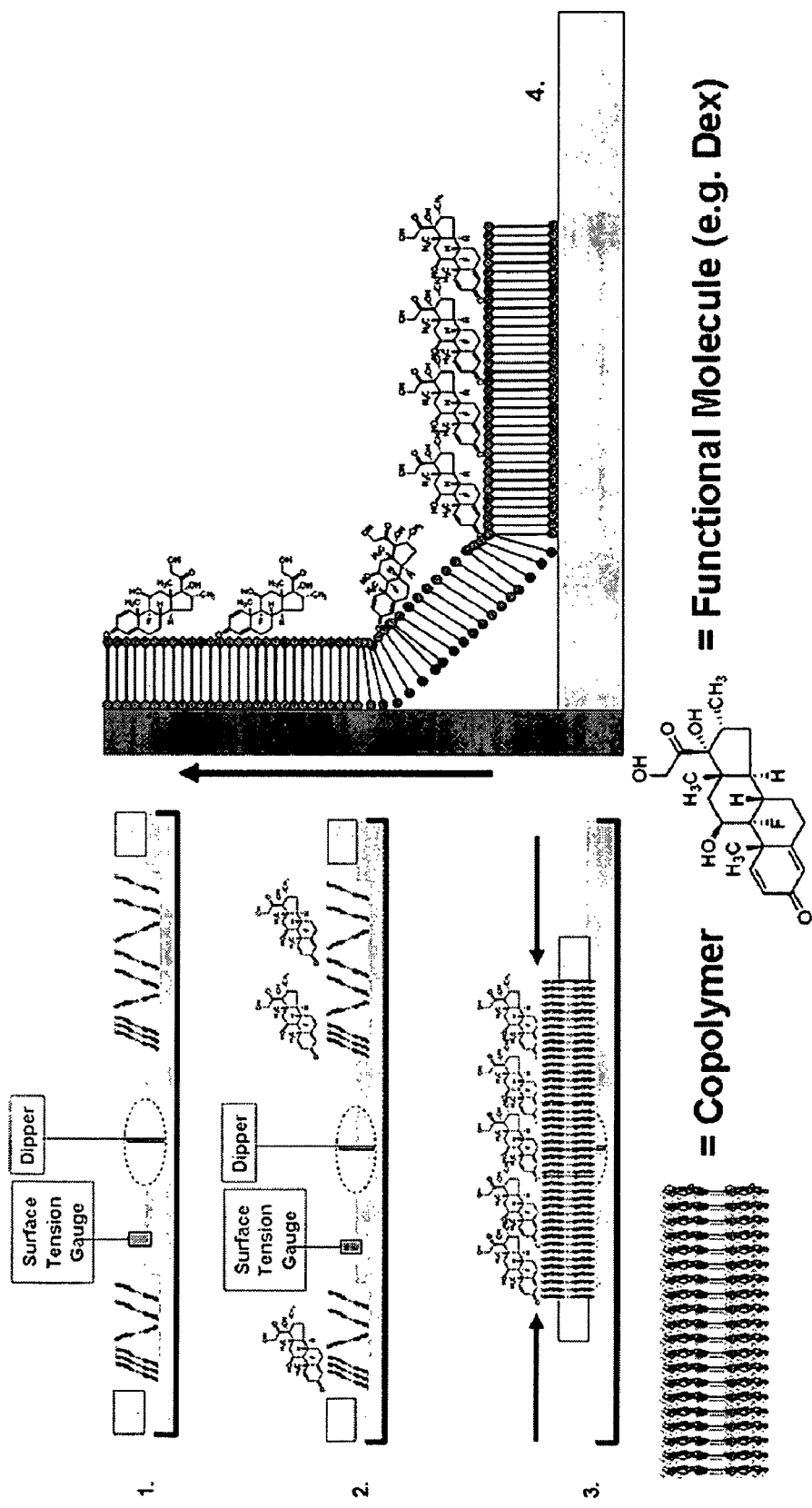
FIG. 1. The process for copolymer-mediated Langmuir-Blodgett deposition is shown here. 1) The copolymer was deposited at the air-water interface to a starting pressure of 10-15mN/m$^2$). 2) The functional molecule (e.g. SWNT or Dex) was added to the surface of the pre-formed membrane in a dropwise fashion to minimize copolymer film perturbation. 3) The film was compressed at a rate of 1 mm/min to fabricate a uniform, tightly packed composite material that could be tethered to the substrate via the copolymer. 4) The deposition process onto the substrate was carried out at a rate of 1 mm/min to ensure complete film formation.

Disclosed herein are functionalized copolymers that provide for tailored biology, where specific functionalities within these materials can be rapidly engineered. Embedding effector molecules into these copolymers transforms an otherwise inactive component into a functional matrix for in vivo applications, including, for example, suppression of cellular inflammation/stress or immuno-regulatory implant coating. Furthermore, the ability to utilize these copolymers in both a vesicular or planar configuration, coupled with their versatility in block composition, allows for dedicated drug delivery with targeting capabilities, or modalities to replenish exhausted effector molecule stores within planar copolymer thin films. As such, these copolymeric membrane materials impact multiple medically-relevant fields in both scientific and technological contexts.

The present inventors have discovered that the materials described herein have bio-inert properties when applied as a thin coating to implantable medical devices. This includes preventing any stress response of macrophages to the chemical/topographical stimuli presented by these materials. In addition to the biocompatibility of the polymers themselves, the present inventors have discovered that various therapeutic agents can be incorporated into the copolymer in order to deliver a therapeutic agent to a tissue.

In one aspect, the present invention provides a nanofilm coating for an implantable medical device (e.g., a stent, or under-skin device, or catheter, or surgical instrument, or implantable device such as a pacemaker, etc.). The term "coating" as used herein, will refer to one or more vehicles (e.g., a system of solutions, mixtures, emulsions, dispersions, blends etc.) used to effectively coat a surface with therapeutic agent and a copolymer component, either individually or in any suitable combination. The present invention further provides a method for using the nanofilm coating to coat a surface with a therapeutic agent, for instance to coat the surface of an implantable medical device in a manner that permits the surface to release the therapeutic agent over time when implanted in vivo.

The coatings include a copolymer complexed with a therapeutic agent in the form of a nanofilm that may be constructed to extremely thin dimensions. In one embodiment, a the thickness of the nanofilms may be from about 0.1 nm to about 20 nm, preferably about 4 nm or less. As such, the coatings can significantly suppress cellular inflammation while possessing dimensions that do not impact the implant with which the coatings are interfaced. These dimensions also enable interfacing with electrodes, or implant leads while still enabling electrode function specifically because the material is so thin and does not preclude electron transport. For example, the present nanofilm coatings may be applied to gold electrodes (e.g., leads) while still supporting oxidation-reduction reactions to occur at the electrode surface.

In some embodiments, multiple layers of the copolymers are used to generate the coatings. Nanofilms can be sequentially deposited to form multilayers to 'tune' the amount of therapeutic agent that has been added to an implant surface. Due to the thin dimensions of each layer in the coating, even coatings made multiple copolymer layers may have a negligible impact upon the device dimensions because each layer may be very thin (e.g., only about 4 nm thick). As such, even a coating that includes 10 copolymer layers, for example, would be orders of magnitude thinner in dimension than a PLGA microsphere.

The coatings may be fabricated/deposited using the Langmuir-Blodgett method which is rapid, low-cost, and accomplished in a parallel fashion with multiple substrates being deposited simultaneously. Furthermore, the materials and deposition modalities employed by this technology enables film deposition on any type of surface or form factor, making this an exceptionally versatile technology that is easily adaptable to multiple applications.

The copolymers in the coating may be di- to tri-block copolymers. Block copolymers have been shown to be effective matrices to support protein function for the mimicry of key natural biological processes such as energy conversion, as well as voltage-gated ion transport [1-7]. While conventional lipid-based systems have enabled single protein characterization and mechanisms of functionality to be elucidated

[8-11], block copolymers represent a highly versatile approach towards nanoscale/engineered medicine, whereby specific properties can be engineered into the material to accommodate specific protein geometries, or desired block lengths, compositions, and charge properties, to name a few. Furthermore, the addition of endgroups, such as acrylate, can be made to enable UV-induced polymeric crosslinking with reported steric contraction of the film to enhance material stability for enhanced device robustness over conventional lipid systems [12, 13]. The copolymeric materials are extremely robust, and can successfully coat a substrate while left in the ambient environment for months. Furthermore, the copolymers are amenable to the demonstrated drug/effector molecule/protein elution studies because they can be crosslinked using both chemical and UV-induced methods. Several polymers/lipids exhibit rapid breakdown when exposed to UV light where interfaced molecules also exhibit breakdown upon degradation of the supporting matrix. In this case, UV crosslinking actually serves as a beneficial condition to further enhance material stability.

In some embodiments, the copolymer is a triblock copolymer and possesses the structure of polymethyloxazoline-polydimethylsiloxane-polymethyloxazoline (PMOXA-PDMS-PMOXA). As noted above, the end groups may be terminated with acrylate, which enables rapid crosslinking to enhance material stability. As previously mentioned, these endgroups can be rapidly functionalized with a spectrum of molecules including membrane proteins (e.g. Bacteriorhodopsin, Cytochrome C Oxidase, etc., as well as effector molecules that suppress cellular processes such as inflammation. Furthermore, the PMOXA endgroup is biologically-inert, meaning it does not freely enter into interactions (e.g., chemical) with its surrounding biological environment. Thus, this material is resistant to cellular adhesion.

The copolymers may optionally be functionalized at the endgroups to enable directed targeting which will enable rapid replenishment of therapeutic agent-depleted nanofilms. More specifically, nanofilm vesicles, or hollow spheres that are carrying a specific drug can have their outside shell functionalized with a receptor, or ligand, that can directly target a planar-deposited film atop an implant that has already eluted the complete stores of the integrated drug. These vesicles can then unravel to restore additional drug into the planar film while providing a very minimal impact upon nanofilm thickness because the material is already inherently extremely thin. As such, this highly versatile material possesses significant improvements over existing films given its several improvements in possessing non-invasive dimensions, interfacing capabilities with a spectrum of molecules, as well as several other key advantages.

Therapeutic agents are incorporated into or complexed with the copolymer such that a therapeutically effective amount of the agent may be delivered to the target site upon implantation of the medical device. A "therapeutically effective amount" of a compound refers to an amount of the compound that alleviates, in whole or in part, symptoms associated with a disorder or disease, or slows or halts further progression or worsening of those symptoms, or prevents or provides prophylaxis for the disease or disorder in a subject at risk for developing the disease or disorder.

The copolymers serve as a platform system, meaning they can be interfaced with a collection of molecules and substances for a wide-array of applications. Virtually any therapeutically active agent for which localized delivery of is desired may be associated with (e.g., complexed with) the copolymer nanofilms in accordance with the present invention. The term "therapeutically active agent" is intended to encompass any substance that will produce a physiological response when administered to a host. Because the triblock copolymer itself has alternating hydrophilic and hydrophobic groups within its structure, both hydrophilic and hydrophobic drugs can be integrated into the copolymer films. Furthermore, crosslinkable endgroups enhance materials robustness and may play a major role in regulating elution rate, as there is a steric hindrance of the film structure which will 'tighten' up the copolymer to reduce drug release.

In general, the term therapeutically active agent includes therapeutic or prophylactic agents in all major therapeutic/prophylactic areas of medicine as well as nutrients, cofactors, and xenobiotics. Suitable substances include, but are not restricted to, antifungals such as amphotericin B, griseofulvin, miconazole, ketoconazole, tioconazole, itraconazole, and fluconazole; antibacterials such as penicillins, cephalosporins, tetracyclines, aminoglycosides, erythromicin, gentamicins, polymyxin B; anti-cancer agents such as 5-fluorouracil, bleomycin, methotrexate, hydroxyurea; antiinflammatories such as glucocorticoids, including dexamethasone, hydrocortisone, colchicine; nonsteroidal antiinflammatory agents including ibuprofen, indomethacin, and piroxicam; antioxidants, such as tocopherols, carotenoids, metal chelators, ubiquinones, or phytate; antihypertensive agents such as prazosin, verapamil, nifedipine, and diltiazem; analgesics such as acetaminophen and aspirin; antiviral agents such as acyclovir, ribavarin, and trifluorothyridine; antiandrogens such as spironolactone; androgens such as testosterone; estrogens such as estradiol; progestins such as modified progestogens; opiates; muscle relaxants such as papaverine; vasodilators such as nitroglycerin; antihistamines such as cyproheptadine; antitussives such as dextromethorphan; neuroleptics such as clozaril; antiarrhythmics; antiepileptics; proteins, polypeptides, neuropeptides such as somatostatin, substance P, vasoactive intestinal peptide (VIP), calcitonin-gene related peptide (CGRP), capsaicin, insulin, and gastrin; and protein enzymes, such as superoxide dismutase or neuroenkephalinase or psychotropics including penothiazines and tricyclics, carbohydrates, glycoproteins, glycolipids, other lipids and cytokines. Cytokines include tumor necrosis factors, the interleukins, growth factors, colony stimulating factors, and interferons. Other useful drugs, in approved commercially available formulations, and their recommended dosages are listed in the annual publication of the Physicians' Desk Reference, published by Medical Economics Company, a division of Litton Industries, Inc.

In an exemplary embodiment, the coatings of the present invention can be interfaced with multiple types of therapeutic agents or drugs including Dexamethasone, which is a glucocorticoid anti-inflammatory molecule that interacts with the glucocorticoid receptor (GR) in the cellular cytoplasm, which then causes the GR to translocate into the nucleus and block the production of cytokines (e.g. indicators of adverse cellular conditions) such as tumor necrosis factor-alpha (TNF-$\alpha$), interleukin-6 (IL-6), interleukin-12 (IL-112), 1P-10, as well as inducible Nitric Oxide Synthase (NOS). Nanofilm materials of the present invention which incorporate Dexamethasone significantly impair the production of these inflammatory molecules. This embodiment of the invention is described in more detail in Example 6, below.

In a second exemplary embodiment, Liver-X-Receptor (LXR) agonists are interfaced with the nanofilm materials of the present invention. LXR agonists are potent inhibitors of LPS-mediated inflammatory responses. Other embodiments include the combination of the polymer with cancer-suppressing as well as bone-growth inducing molecules for their respective applications in cancer therapeutics, as well as seeding bone growth for dental and orthopedic implants.

Recent studies have been done on natural polymers in the field of tissue engineering with hopes to mimic nature [19B]. However, these natural polymers alone cannot be incorporated as a coating because they are often only a few nanometers thick. In the past, the triblock copolymer used in the conventional APC membranes, though effective as a nano scale drug molecule reservoir, was very difficult to manually handle and therefore, was challenging to use in a clinical setting as a stand-along device or patch and is generally applicable as a drug eluting coating. Inability to manually handle tri-block copolymer in the conventional APC membranes were addressed by incorporating parylene, an extremely conformal FDA approved bio-inert polymer, as a backbone for the drug/copolymer layer [20B, 21B].

In another exemplary embodiment, Dex was successfully conjugated to the copolymer matrix; the presence of Dex was confirmed through extensive gene expression studies that illustrate the inflammatory response was significantly abated in macrophages cultured on the APC membrane versus plain glass and plain parylene (Example 8, below) therefore, the APC membrane can serve as an effective drug carrying interface for the purpose of coating implants, or directed drug delivery. In addition, this embodiment demonstrates tunable slow release capabilities of the APC membrane by incorporating an ultra-thin parylene layer that contains nanopores. The presence of these nanopores has been confirmed through AFM images and slow-elution properties were apparent from gene expression studies (Example 8, below). The nanopore parylene layer is important to the APC membrane because it acts as a semi-permeable membrane through which pharmaceutical agents may slowly diffuse. Without the porous layer, drug delivery would not be localized and have absolutely no long-term value to the patient due to immediate exposure and dilution of the drug through the patient's whole system; such a result would have severe medical complications especially with anti-inflammatory and chemotherapeutic agents that are universally cytotoxic [22B]. The importance of localized drug delivery is unparalleled in overcoming numerous ailments including cancer, infections, and aggressive immune responses. Several criteria that should be considered when constructing a novel coating include biocompatibility, preserved efficacy, and longevity. This strategy enables the APC membrane to satisfy these criteria through focusing on using biocompatible materials such as parylene, which has an extended shelf-life lasting many years due to its enhanced biostability [23B].

In the related aspect, the membrane has been engineered with slow-elution capabilities to maximize exposure to the effective dose for the maximum amount of time. Most importantly, these properties have combined into one single entity to serve as a flexible platform for drug delivery capable of diverse application as a pharmaceutical agent transplant, device coating, drug-eluting patch, and tissue regeneration scaffold among others. Therefore, the APC membrane disclosed herein satisfies the criteria necessary for a biomedical membranes, and offers a significant advantage over contemporary methods of drug delivery and modern biomedical coatings due to its ability to slow-release a plethora of pharmaceutical agents, localize drug delivery, and conform to virtually any device surface giving it even greater potential to be incorporated into future biomedical devices.

Experiments conducted during the development of the present invention also showed that nanofilms of the present invention were non-toxic. In particular, in a mouse liver toxicity model injected with high concentrations of nanofilm showed favorable, non-toxic results.

In certain embodiments, the compositions of the present invention are used as a nutrient delivery wrap for plants. In other embodiments, the compositions of the present invention are used to treat hepatitis by allowing sustained release of interferon (e.g., in a subdermal/subcutaneous configuration). In some embodiments, the compositions of the present invention are used on the skin for tattoo removal. In further embodiments, the compositions of the present invention are used for space medicine (e.g., transdermal release of nutrients). In particular embodiments, the compositions of the present invention are employed for veterinary purposes, such as treating cancer and infection by helping to reduce toxicity and enhance efficacy.

In certain embodiments, commercial applications include the application of the nanofilm technology as cardiovascular and neural implant coatings, lead and stent coatings, dental implant coatings, as well as orthopedic implant coatings. The nanofilm compositions of the present invention allow interfacing of the anti-inflammatory/anti-cell adhesion nanofilm with implant surfaces due to its demonstration as an effective suppressor of macrophage adhesion/recruitment in vivo. This ability plays a key role towards the enhancement of implant chronicity in functionality, or how long the implant is able to function while resisting impairment by macrophage aggregation. In addition, in certain embodiments, the nanofilm can be interfaced with leads and stents because it can still enable normal electrode function due to its very thin dimensions. As such, this nanofilm serves as a highly efficient modality for the localized suppression of cellular inflammation which in an applications context can combat the implant fouling process. The highly versatile and robust nature of the polymer also allows for vesicular targeting to replenish polymeric films that have completed the drug elution process. This very robust material can also be applied towards the coating of dental implants as current technology results in the imminent breakdown of the implant due to fouling of the implant-bone interface. This polymer could be integrated with bone growth-promoting molecules (e.g. bone morphogenic proteins) to form highly robust interfaces to promote bone growth. Because block copolymers are already used as ingredients in toothpastes, precedent already exists with respects to the FDA approval process for this material. Furthermore, a substantial amount of investment has been provided by private corporations, as well as the federal government across all major agencies (e.g. NIH, NSF, DoD, etc.) to develop the next generation of implant technologies for neuromedicine, cardiomedicine, and wireless health monitoring. At the interface of this emerging class of implantables, and chronic functionality within the human body will be the nanofilm material of the present invention which can be integrated with all of these technologies and will hence, serve as a gateway material to empower this new class of implants to function with unparalleled fouling resistance capabilities.

For the purposes of this disclosure and unless otherwise specified, "a" or "an" means "one or more"

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1

Polymer Preparation and Characterization

The PEO-PMMA and PMOXA-PDMS-PMOXA copolymers were solubilized to 0.1 mg/ml in chloroform and stirred overnight to result in a translucent, homogeneous solution for LB deposition. The thickness of the materials may be characterized, using a PMOXA-PDMS-PMOXA triblock structure as an example, by performing a secondary treatment of the chloroform-solubilized copolymer with toluene and suspending a droplet across a 25 µm-thick hydrophobic septum flanked by 2 Ag/AgCl electrodes for capacitance measurements as given by: $C = \epsilon_o \epsilon_1 A/d$, where C is the membrane capacitance, $\epsilon_0$ is the permittivity of free space (=8.9×10-19 F/m), $\epsilon_1$ is the relative dielectric constant of the PDMS hydrophobic block, A is the measured area of the annulus in the septum (=250 µm), and d is the thickness of the membrane. The resultant thickness of the materials were determined to range between 3-4 nm [14-16] for the triblock structure. As such, we expected the diblock copolymer to possess a thickness with an upper limit of ~3 nm.

Example 2

General Langmuir-Blodgett Film Fabrication Protocol for Polymeric Substrates

LB films were fabricated using a KSV 2000 Standard Langmuir Trough with a Teflon® base and a subphase of water. To preclude sample contamination from ambient particles, the entire trough was covered with a plastic case and a small door was integrated to allow for manual manipulation/cleaning of the trough. The base was cleaned with chloroform using a cotton swab and large tweezers and then rinsed thoroughly with nanopure water. The water was then swept using cotton swabs into the central reservoir of the trough and suctioned off using a vacuum pump. This step was performed three times to ensure trough cleanliness. The trough was then filled with nanopure water while paying careful attention not to deposit water droplets along the edge of the trough. The Wilhemy platinum pressure sensing plate (stored in MeOH was then thoroughly rinsed using nanopure water, and subsequently sterilized using a torch. The pressure sensor was then zeroed and the ready for film deposition (FIG. 1).

Example 3

Single-Walled Carbon Nanotube Preparation/Deposition for Bioelectricity Measurements Single walled carbon nanotubes (SWNT) (Sigma-Aldrich, Inc. St. Louis, Mo., USA) were solubilized to 1 mg/ml in chloroform with overnight stirring. Following the addition of PEO-PMMA or PMOXA-PDMS-PMOXA polymer solutions onto the Langmuir trough to a starting pressure of 15-20mN/m, the SWNT's were then added in a dropwise fashion to minimize Langmuir film perturbation. Changes in surface pressure as a result of SWNT addition were noted and following 30 minutes to allow for the film to reach equilibrium, compressions were performed at a rate of 1 mm/min to maximum pressures of 30-40mN/m for LB deposition onto gold-coated glass slides at a rate of 1 mm/min. (VWR Scientific, Inc.) (Films were compressed to >50mN/m until collapse for Langmuir film characterization of film properties). Gold coated slides were utilized in this case as the SWNT films were used to enhance electron harvesting capabilities for the gold working electrode measurement of cytochrome c-mediated oxidation-reduction. For the SWNT-copolymer experiments, variations to the film deposition as well as preparation methods were also employed given that the SWNT's were also soluble in chloroform, and for the purposes of cytochrome c activity measurement the PEO-PMMA/PMOXA-PDMS-PMOXA copolymers also possessed anti-protein adsorption capabilities to facilitate electron transfer. A down-dip method was also employed where the substrate was lowered into the trough such that the floating Langmuir film facing the air was deposited directly onto the substrate, while the side facing the subphase became the top layer after deposition onto the substrate. Chloroform-solubilized SWNT/Copolymer solutions were also deposited at the air-water interface. For oxidation-reduction measurement, 30 mg of cytochrome c (Horse heart muscle, Sigma-Aldrich, Inc. St. Louis, Mo., USA) was dissolved in 2462.5 µl of water (Nanopure). 37.5 µl of a 1 mg/ml solution of ferricyanide (Sigma-Aldrich, Inc.) was then added to the cytochrome c solution. This composite solution was then added to a Desalting column (Amersham Biosciences) to complete the process to produce CytC3+. The oxidized CytC was then concentrated down in a swing bucket rotor at 4000g and 4° C. to a final volume of 250-300 µl.

Cyclic voltammetry was performed using an electrochemical workstation (Solartron, Inc.). Platinum, gold, and a saturated Ag/AgCl (205 mV vs SHE) were used as the counter, working, and reference electrodes, respectively. A buffer of 20 mM Mops, pH 7.0, 50 mM Na2SO4, 50 mM K2SO4, 2.5 mM MgSO4, 0.2 mM EDTA was prepared for CV experiments. Experiments were performed at a scan rate of 30 mV/s between −0.18V and 0.5V versus open circuit.

Example 4

Glucocorticoid Preparation/Deposition for Inflammation Attenuation Studies

Figure 6:
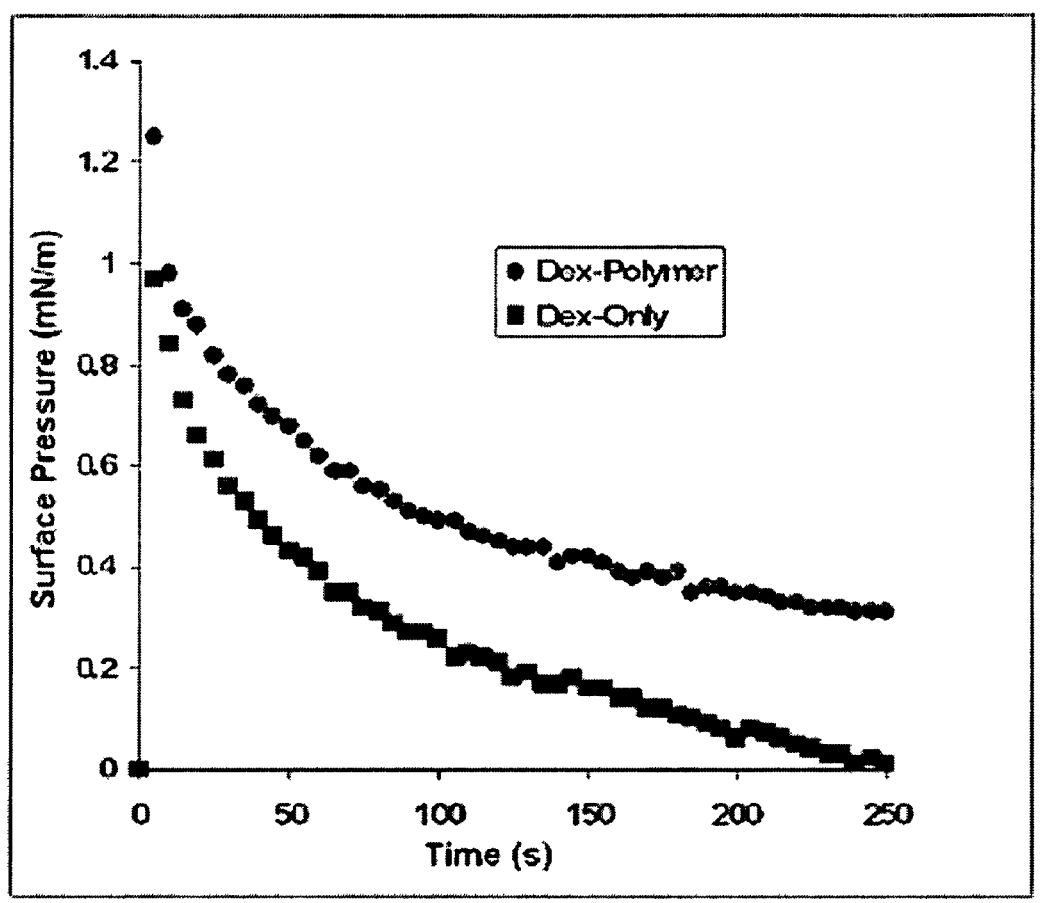
FIG. 6. Water-soluble Dex deposited atop the copolymer was suspended at the surface of the Langmuir trough and integrated with the copolymer (circle) while Dex was shown to submerse into the subphase when deposited without the copolymer (square).
Figure 7:
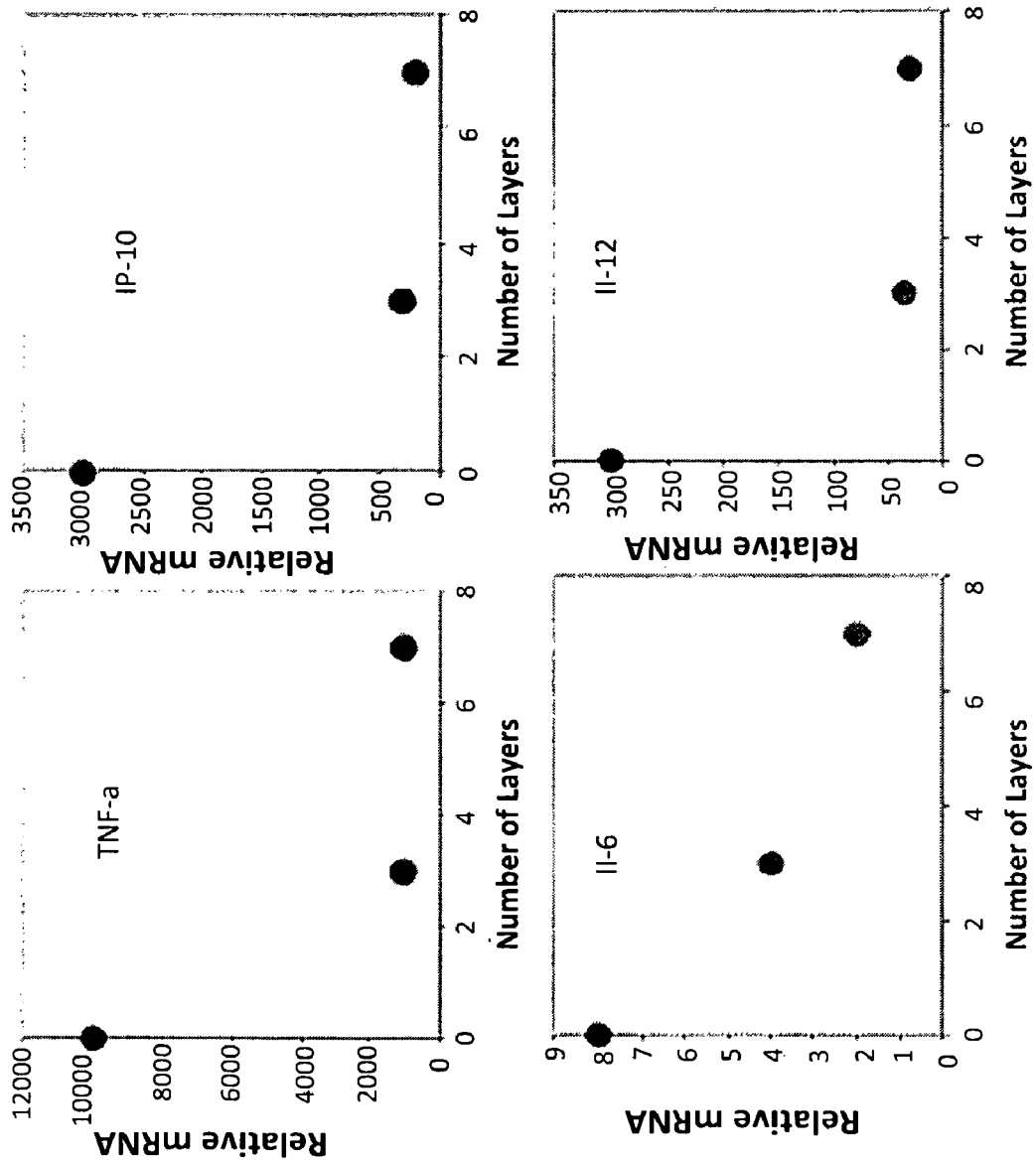
FIG. 7 RT-PCR examination TNF-α, IP-10, 11-6, and 11-12 mRNA show major reductions in inflammation based on the number of DEX-films deposited. These films may be useful towards eliminating initial onset of cellular inflammation that may trigger device fouling.
Figure 8:
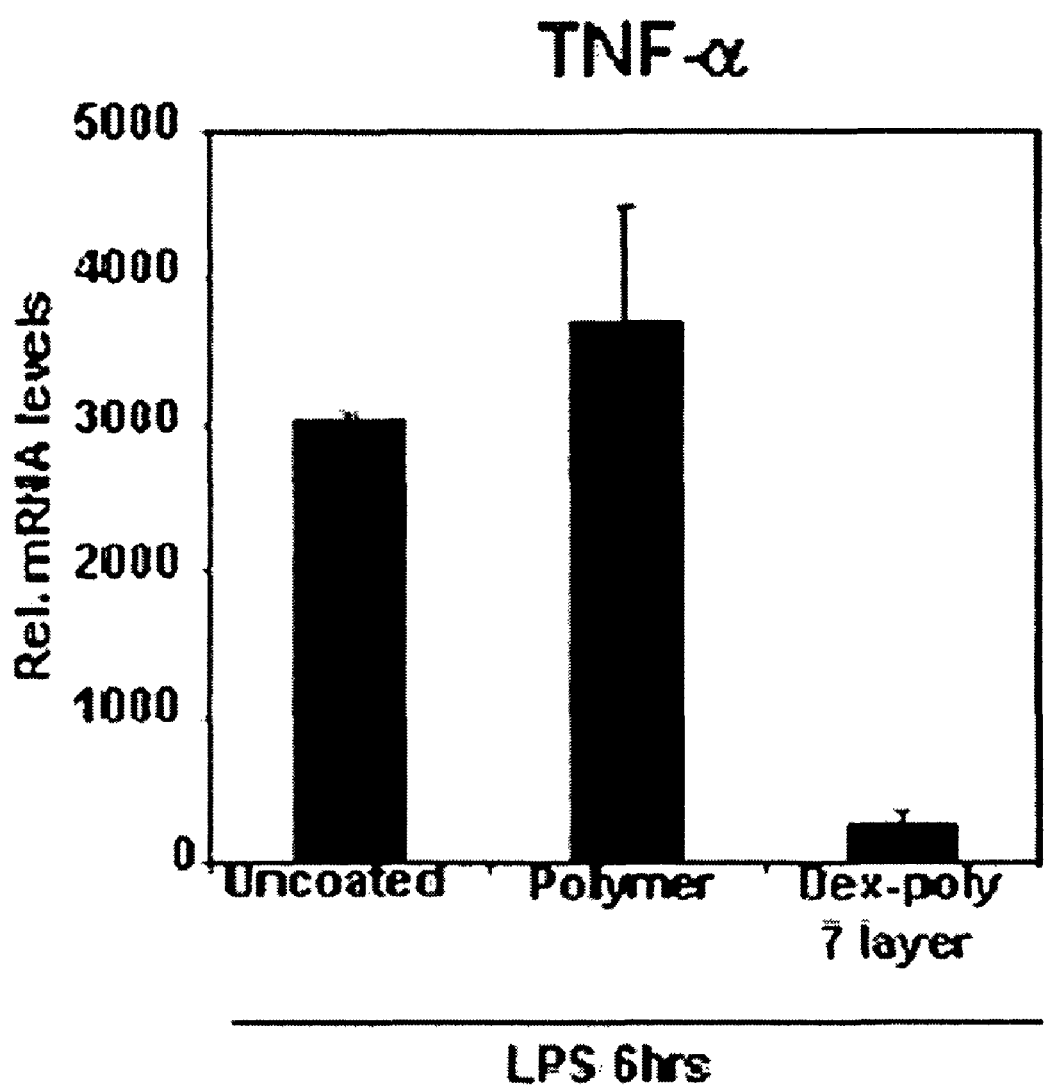
FIG. 8. Dex-functionalized films show an early complete suppression of TNF production from RAW cells.
Figure 9:
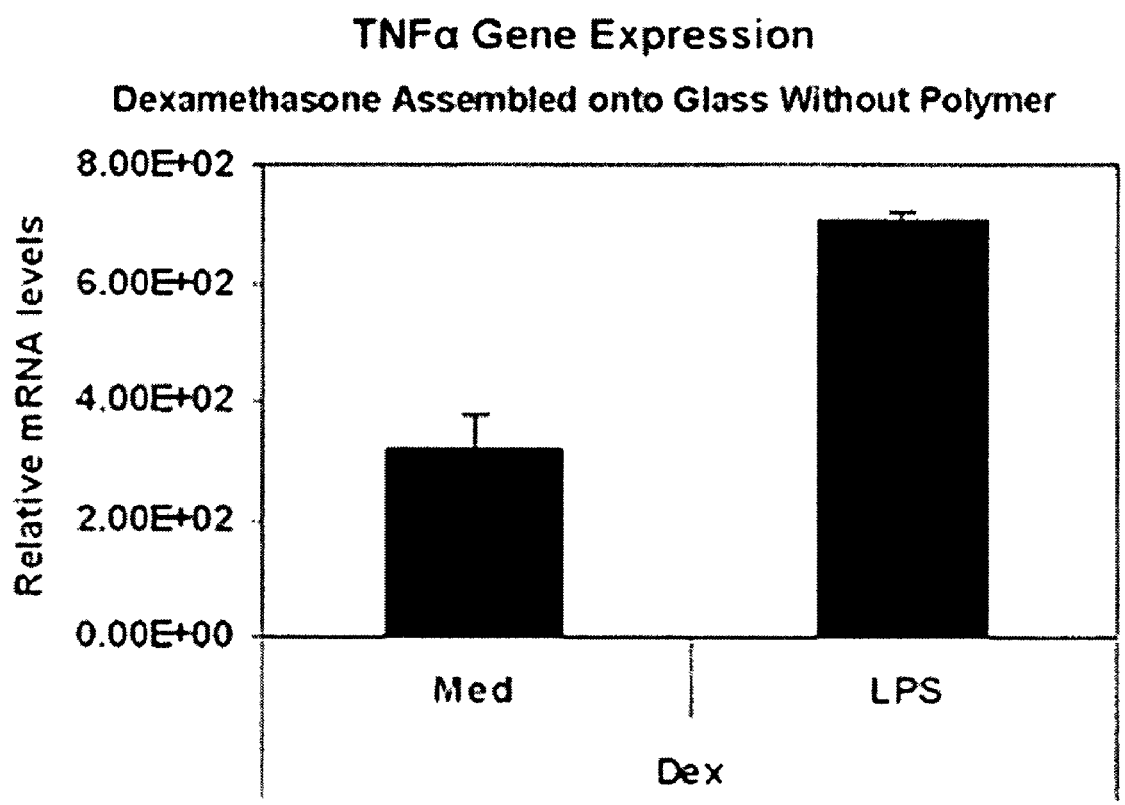
FIG. 9. For samples where Dex was self-assembled onto the glass substrate without the polymer, it could be seen that stress attenuation was precluded. This showed that the copolymer enabled both interfacial Dex deposition as well as the ability to tether the Dex to the substrate and sustain the interface between the macrophages and anti-inflammation capabilities of the composite material.

Water soluble dexamethasone (Sigma-Aldrich, Inc.) was dissolved in nanopure water to a concentration of 1 mg/ml. The drug was then added to an interfacial pre-formed 10mN/m copolymer film and changes in surface pressure were monitored to confirm dexamethasone presence at the air-water interface. After 30 minutes of allowing the film to reach equilibrium, compressions were also performed at a rate of 1 mm/min (FIG. 6) to a maximum pressure of 30 mN/m for LB deposition onto glass slides (25 mm×75 mm) at a rate of 1 mm/min. (VWR Scientific, Inc.) (Films were also compressed to >50mN/m until collapse for Langmuir film characterization of film properties). The slides were then used for Raw 264.7 murine macrophage culture and quantitative Polymerase Chain Reaction (qPCR) analysis.

Raw 264.7 (ATCC) were cultured at 37° C. in DMEM supplemented with 10% FBS and 5% Penicillin/Streptomycin. Following the acquisition of cultures of adequate density, cells cultured on bare glass as well as the composite films were exposed to lipopolysaccharide (LPS) for 4 hours, and slides were subsequently transferred to new Petri dishes and 1 ml of TRIzol cell lysis solution was added to wash the slides and collect the genetic material. RNA isolation was done according to the manufacturer's protocol. Subsequent conversion of the RNA to cDNA was performed using the I-script enzyme (Bio-Rad) (Applequist et al., 2002. International Immunity 9:1065-1074; Perry et al., 2004. The Journal of experimental medicine. 199:1651-1658; Doyle et al., 2003. Journal of immunology 170:3565-3571).

Following conversion of the isolated mRNA to cDNA, qPCR analysis (Bio-Rad, Richmond, Calif., USA) was performed to examine the expression of tumor necrosis factor-alpha (TNFα), following LPS induction both with and without dexamethasone activity.

Example 5

SWNT-Copolymer Deposition for Bioelectric Measurement

Figure 2:
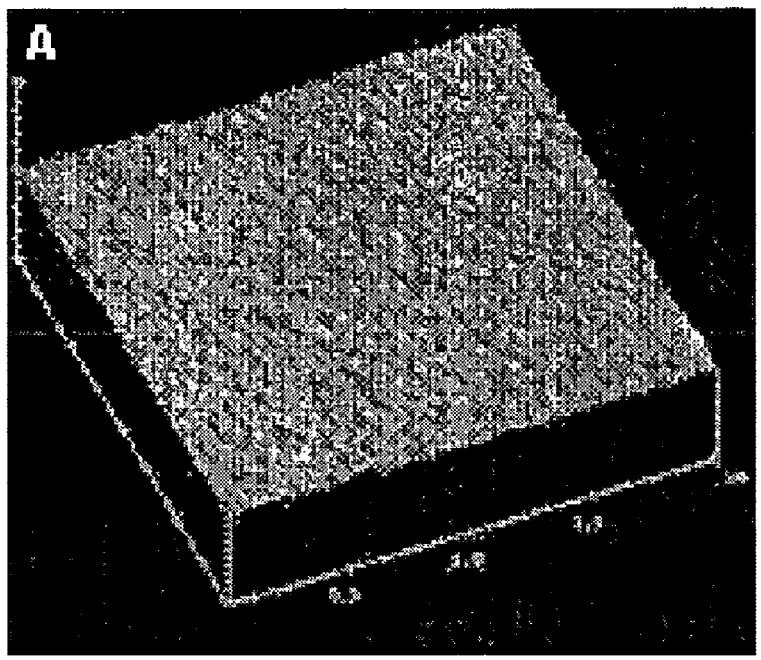
FIG. 2A. Tapping mode atomic force microscopy was utilized for LB film imagery. An AFM micrograph is shown here with a scan size of 2 μm at a frequency of 0.7016 Hz. The copolymer nanofilm exhibited a very robust adhesion to the glass substrate.
FIG. 2B. A scan of a SWNT-Copolymer composite film is shown here with a scan size of 0.4922 μm with a scan rate of 1.001 Hz. The presence of SWNT's integrated with the copolymer molecules was also confirmed via Langmuir isotherm analysis as well as cyclic voltammetric measurement of cytochrome c-mediated oxidation-reduction reactions (triblock).
Figure 2:
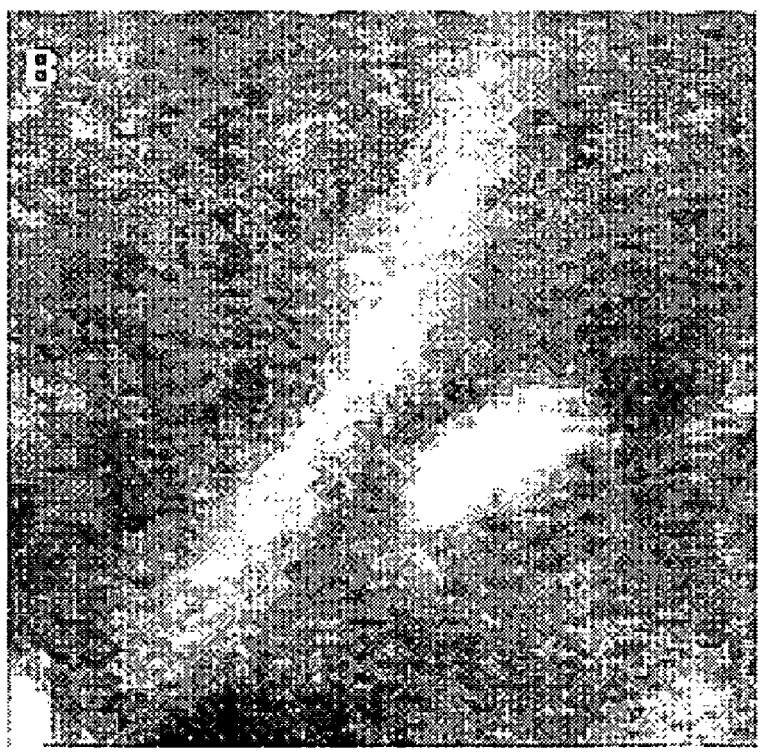
Figure 3:
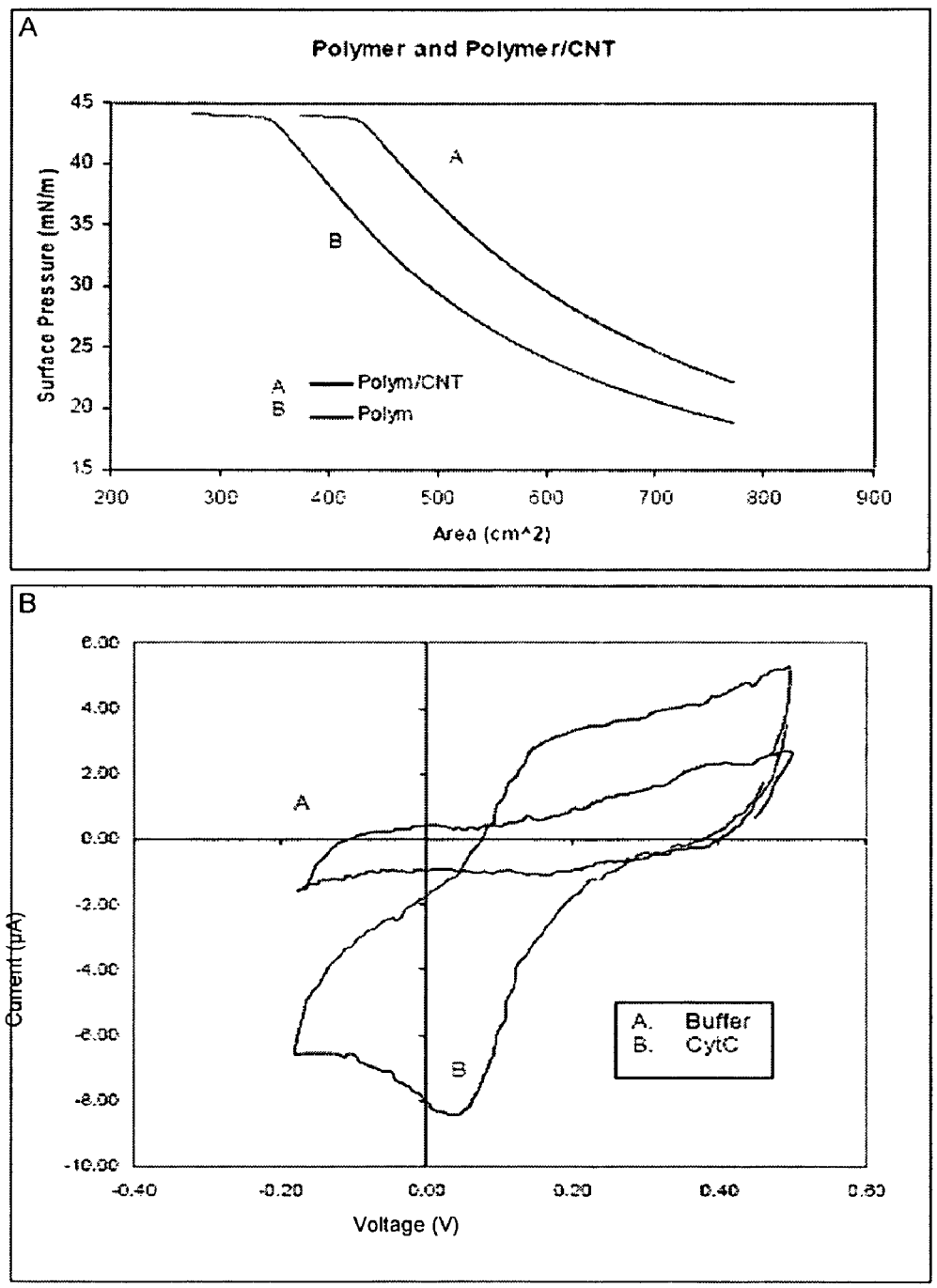
FIG. 3A. Langmuir isotherm is shown here comparing measurements for polymer-only films with SWNT-Copolymer films. It can be seen that composite films exhibit a higher surface pressure versus trough area indicating the presence of SWNT's at the air-water interface.
FIG. 3B. Cyclic Voltammetry further confirmed the functional presence of SWNT's as well as the anti-adsorption abilities of the copolymer via measurement of cytochrome c-mediated electron transfer to an underlying gold electrode which served as the substrate for composite film deposition (triblock).

Atomic force microscopy was utilized to image the polymeric nanofilm substrates as well as analyze SWNT deposition (FIGS. 2A/2B). FIG. 2A represents an AFM micrograph with a scan size of 2 μm at a frequency of 0.7016 Hz. FIG. 2B represents an AFM micrograph of a SWNT deposited at the air-water interface. In addition to AFM analysis, Langmuir isotherms were performed for polymer-only membranes as well as films containing both the polymer and the SWNT's (FIGS. 3A/B). FIG. 3A shows an increase in surface pressure versus trough area for the SWNT-containing film indicating the presence of the nanostructures along with the PMOXA-PDMA-PMOXA copolymer molecules at the air-water interface. In addition, the compression isotherm data indicates that carbon nanotubes are interacting with the polymer blocks at the air-water interface and not completely falling into the subphase. The polymer solution was spread at the surface and a compression isotherm was run. The barriers were relaxed and SWNT's solubilized in chloroform were spread across the air-water interface, resulting in a slight rise in the surface pressure, indicating an increase in the mean molecular area at the air-water interface. This data suggests that a portion of the SWNT's remained at the surface, possibly due to an interaction with the hydrophobic block of the copolymer for substrate deposition.

The greatest current output occurred when polymer/SWNT films were deposited by the down dip method (FIG. 3B). In this method, the substrate was lowered into the trough such that the floating Langmuir film facing the air is deposited directly onto the substrate, while the side facing the subphase becomes the top layer once deposited onto the substrate. As previously mentioned, to further ensure a high density of SWNT's in the film, polymer and carbon nanotubes were incubated and dissolved into the same chloroform solvent prior to spreading. After spreading the polymer/SWNT solution on top of the subphase, additional SWNT solution was spread across the surface. The film was compressed to 30mN/m, and additional SWNT solution was spread on top of the film. It was believed that the compressed polymer film could sustain the additional deposited SWNT's, such that during the down dip method, a layer of SWNTs can be directly deposited onto the gold electrode. SWNT solution was added until the chloroform no longer spread rapidly across the surface, indicating that the surface was saturated. The floating film was then compressed to 40mN/m for deposition onto a gold electrode. Cyclic voltammetry (CV) analysis of cytochrome c-mediated electron transfer to the carbon nanotube films resulted in high current outputs. It was found that incorporating SWNT's into the polymer membrane could improve the conductivity of the polymer while maintaining both anodic and cathodic current peaks. In addition, the presence of the copolymer was believed to play an additional role to supporting SWNT interfacial deposition. As the stability of the cytochrome c-gold interaction was previously shown to be influenced by the unperturbed interaction between the protein, buffer, and electrode by preventing the adsorption of protein to the electrode which in turn precludes high fidelity electron transfer and reaction reversibility, the hydrophilic copolymer endgroups were believed to play an important role in precluding cytochrome c adsorption much like previous reports of using hydroxythiol (HT) self assembled monolayers [20,21].

Example 6

Glucocorticoid-Copolymer Films for the Study of Cellular Inflammation

Figure 4:
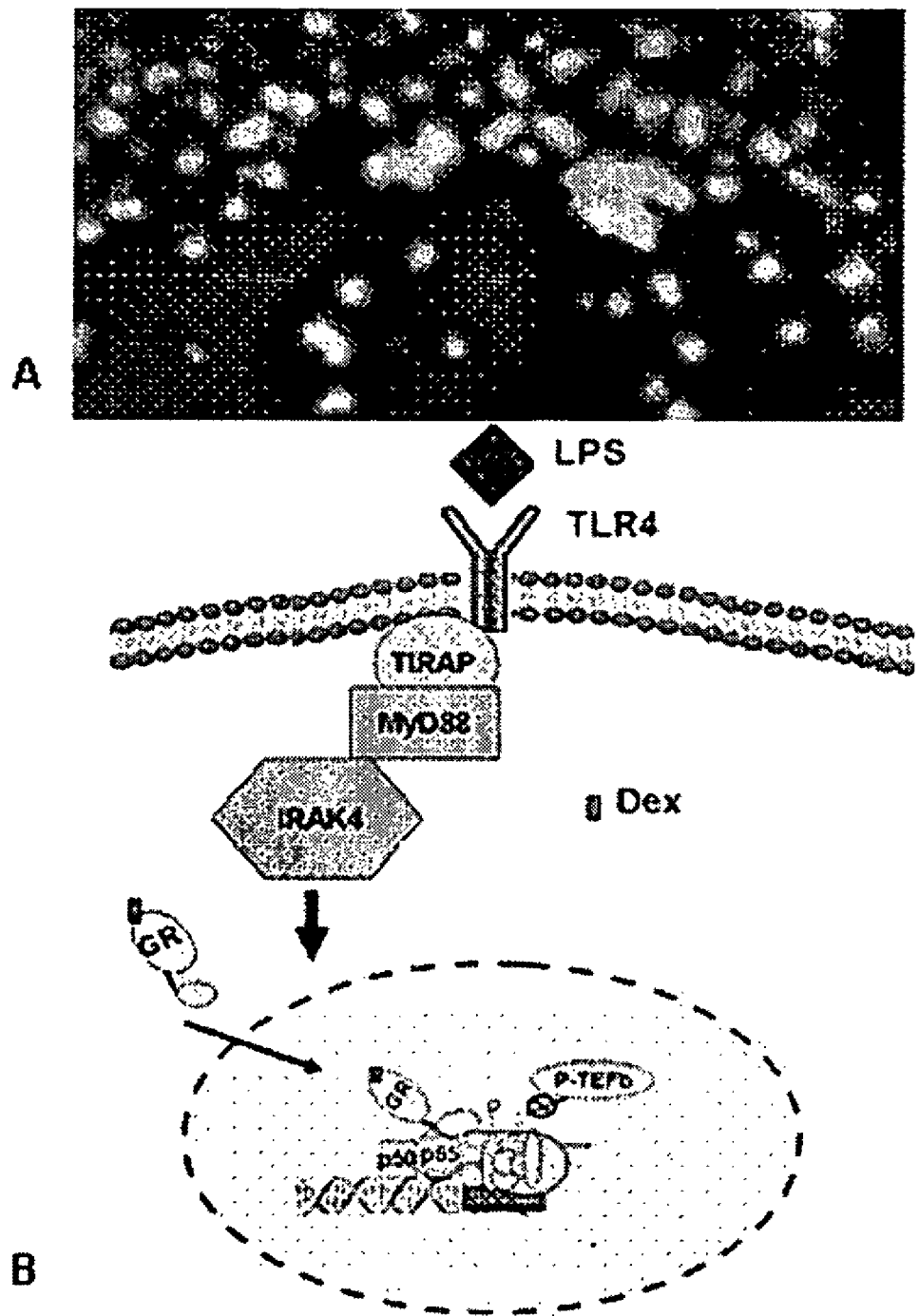
FIG. 4A. FITC-Dex complexes were deposited atop PEO-PMMA copolymers and fluorescence imagery was performed to examine Dex transfer onto the substrate. Amphiphile-assisted Dex deposition resulted in the transfer of the drug to the substrate while deposition of Dex alone did not result in its transfer.
FIG. 4B. Application of LPS to the Raw 264.7 macrophages resulted in the induction of p65-mediated inflammatory gene programs which were targeted by the Dex-Copolymer composites to attenuate cell stress (diblock).

Dexamethasone (Dex) deposition was conducted atop both the PEO-PMMA/PMOXA-PDMS-PMOXA copolymers. Dex presence was confirmed via the application of a FITC-Dex compound atop the pre-formed copolymer monolayer (FIG. 4A). FITC-Dex added without the copolymer resulted in the inability to transfer the anti-inflammatory to solid substrates following film compression (Data not shown).

Figure 5:
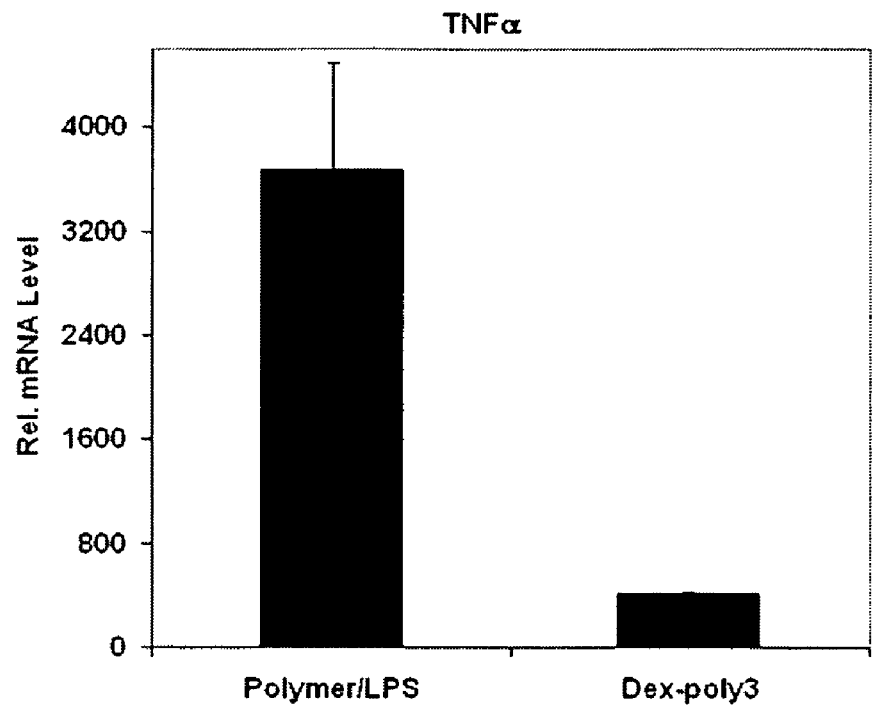
FIG. 5A. Using TNFα as an example of a cytokine that was expressed as a result of LPS induction, it could be seen that cells cultured atop the composite films showed significant reductions in inflammation compared to cells cultured atop the polymer and stimulated with LPS.
FIG. 5B. Incubation of the Raw 264.7 macrophage cell line with a 0.1 g/ml of copolymer in solution did not affect cell growth behavior nor did the incubation affect cell growth rates. Images were taken at 4 hrs, 24 hrs, and 48 hrs. This observation was an indication that the copolymer was biologically inert with no qualitative adverse effects upon cellular behavior.
Figure 5:
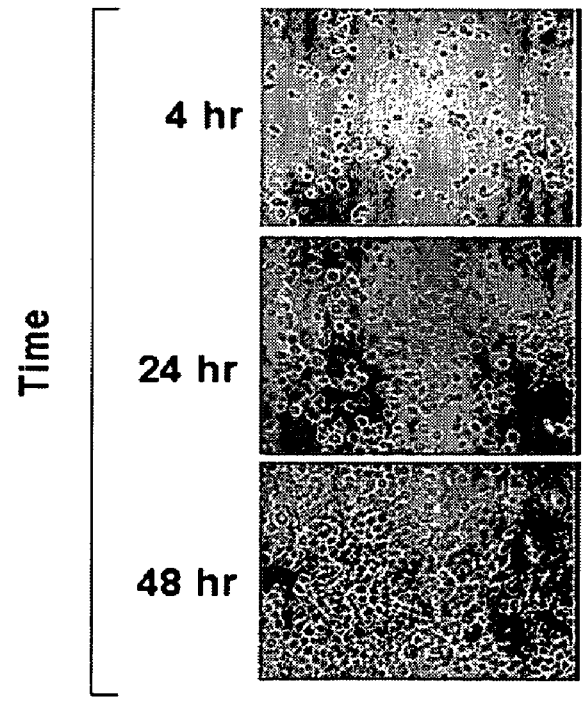
Figure 10:
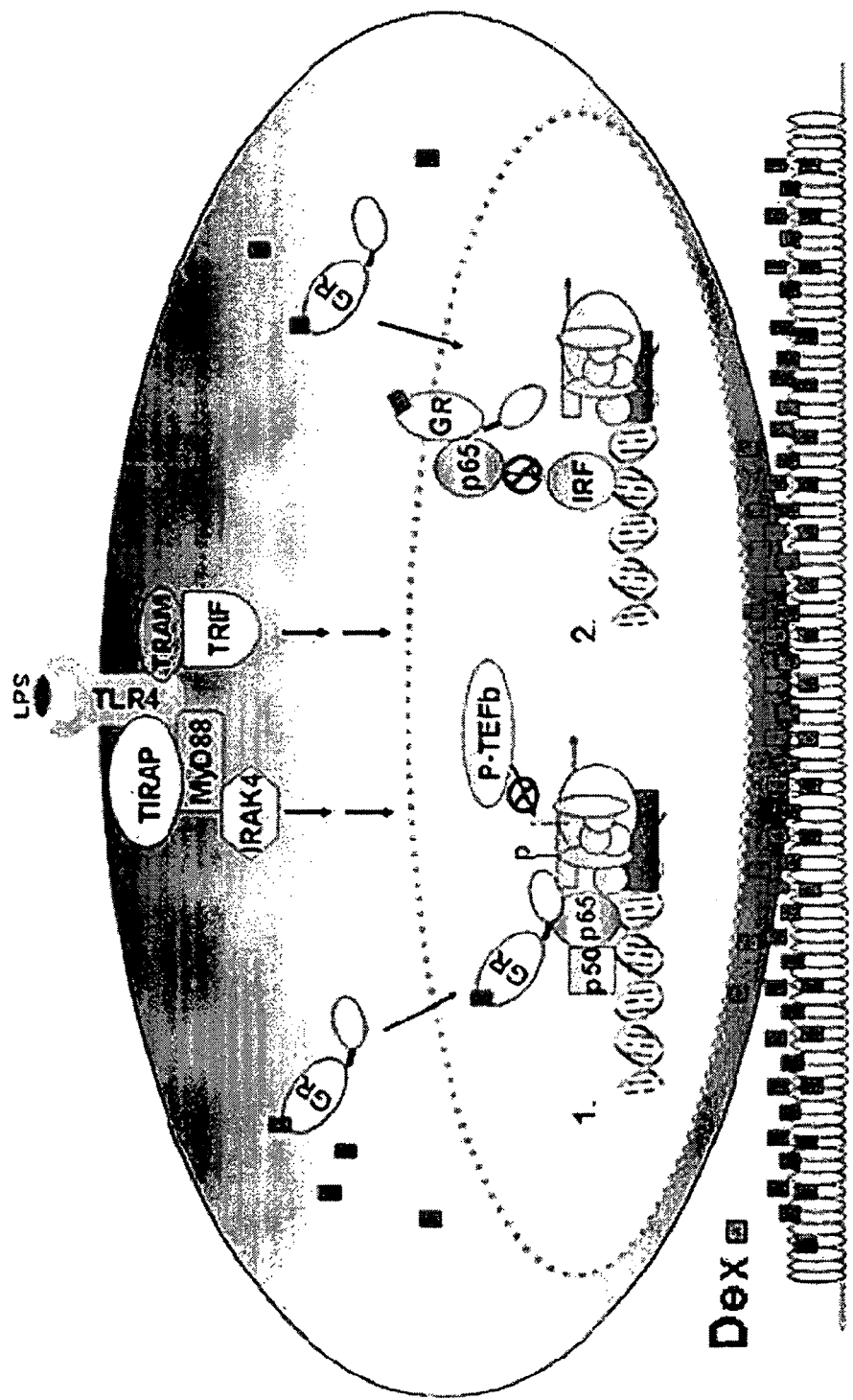
FIG. 10 illustrates drug elution from a nanofilm into macrophages. Immobilized dexamethasone was shown to exhibit internalization capabilities following in vitro cell culture. Dexamethasone is known to enter into a binding relationship with the nuclear glucocorticoid receptor whereby Dex-GR complex binding with p65 interferes with p65 interaction with transcriptional machinery for inflammatory cytokines. Evidence also shows that p65 interaction with co-activators is also blocked via Dex-GR binding.
Figure 11:
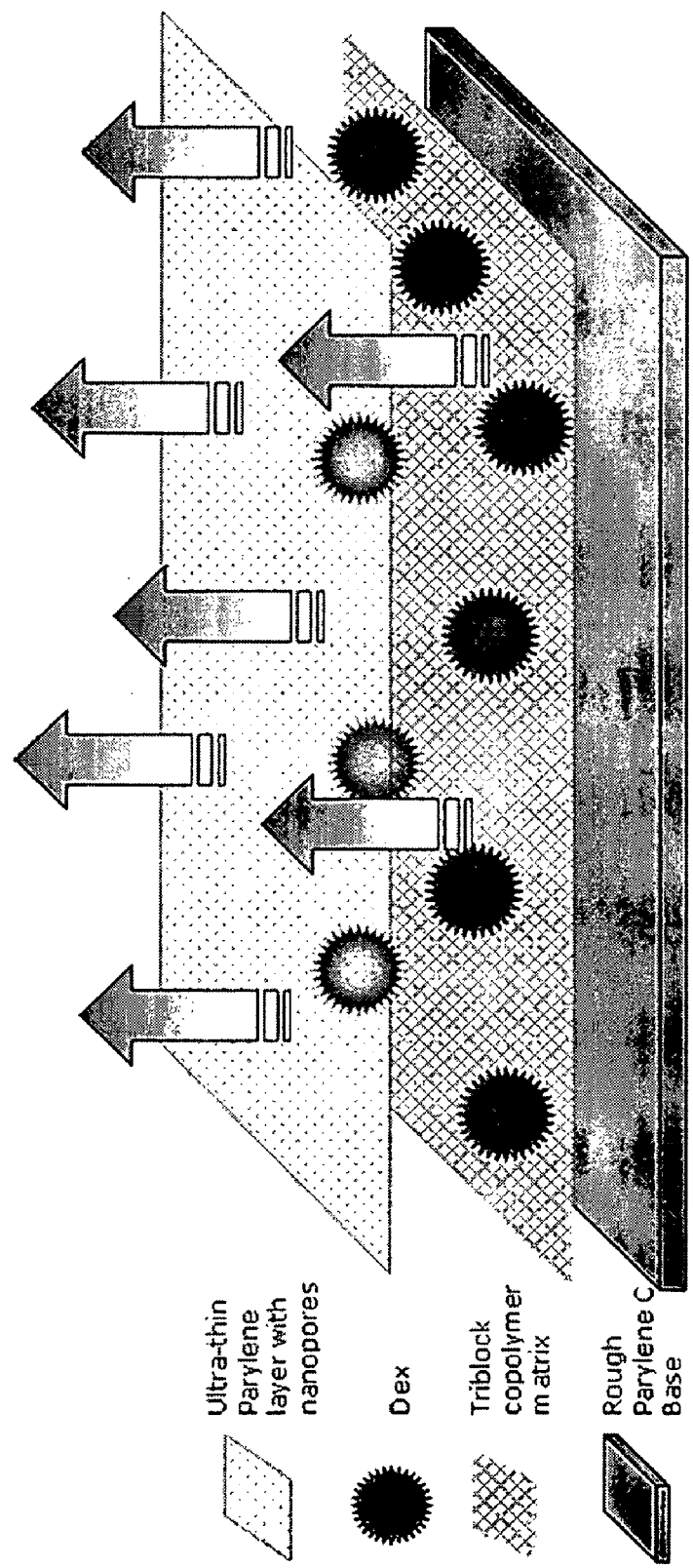
FIG. 11. Cross-section view of an APC membrane. The base layer is a layer of parylene that serves as the backbone of the membrane. The top layer is a layer of ultra-thin parylene with nanopores that acts as a semi-permeable membrane. Sandwiched between the parylene layers is a tri-block copolymer matrix that can be rapidly functionalized with molecules. The drug used in one embodiment was dexamethasone (Dex), which was incorporated into the tri-block copolymer matrix and deposited onto the parylene base layer with a Langmuir-Blodgett trough. The figure shows drug eluting through the nanopore layer by diffusing across the membrane. The size of the nanopores may be engineered to control the rate of drug elution. Multiple layers of the Dex/tri-block copolymer matrix may be applied at the cost of only a few nanometers to extend the bio-longevity of the membrane for many more hours or even days.
Figure 12:
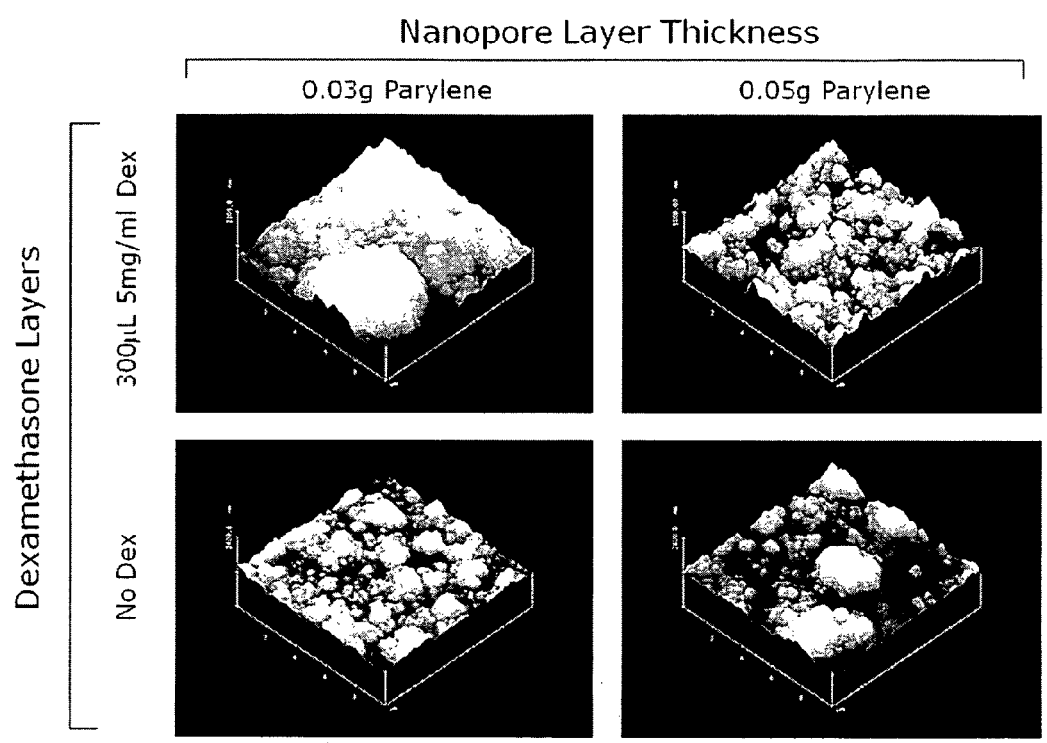
FIG. 12. AFM images of APC membrane surfaces (top) and parylene only surfaces (bottom) at two different nanopore layer thicknesses. Depressions are shown on the surface of the membranes as darker areas suggesting possible nanopore formation. The geography of parylene exhibits rough terrain capable of acting as an inflammatory stimuli.
Figure 13:
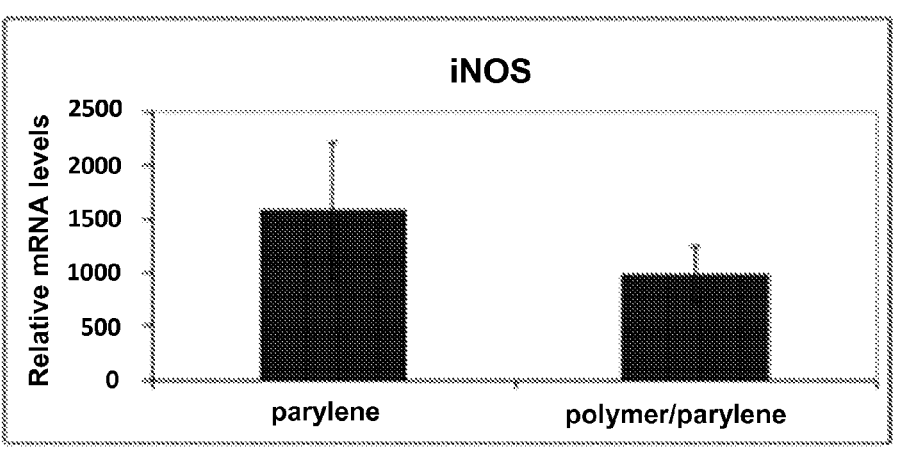
FIG. 13A. Cellular expression levels for iNOS were shown to decrease when RAW264.7 cells were cultured atop parylene copolymer composite surfaces versus being cultured atop bare nanostructmed parylene.
FIG. 13B. Cellular expression levels for TNFa were shown to decrease when RAW264.7 cells were cultured atop parylene-copolymer composite surfaces versus being cultured atop bare nanostructured parylene. These results indicate that murine macrophages can possibly sense their substrate stiffness to elicit innate inflammatory responses as polymer-coated parylene may present a more biomimetic interface with the cells. AFM images indicated that a bare parylene surface contained micro/nano-structured features that could serve as inflammatory stimuli.
Figure 13:
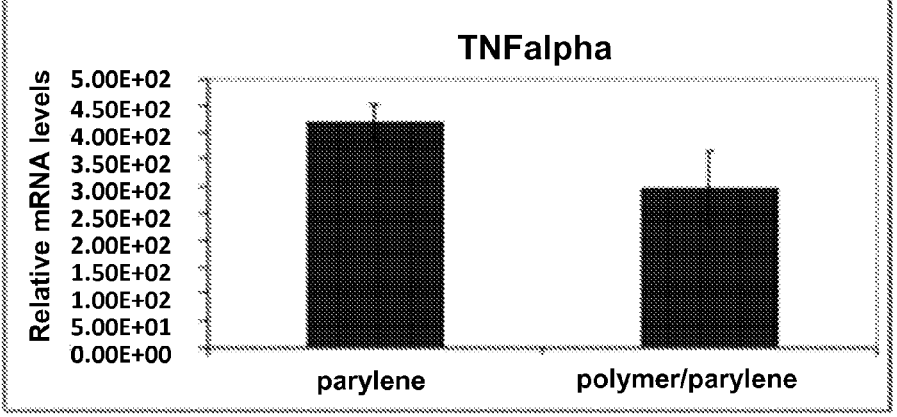
Figure 14:
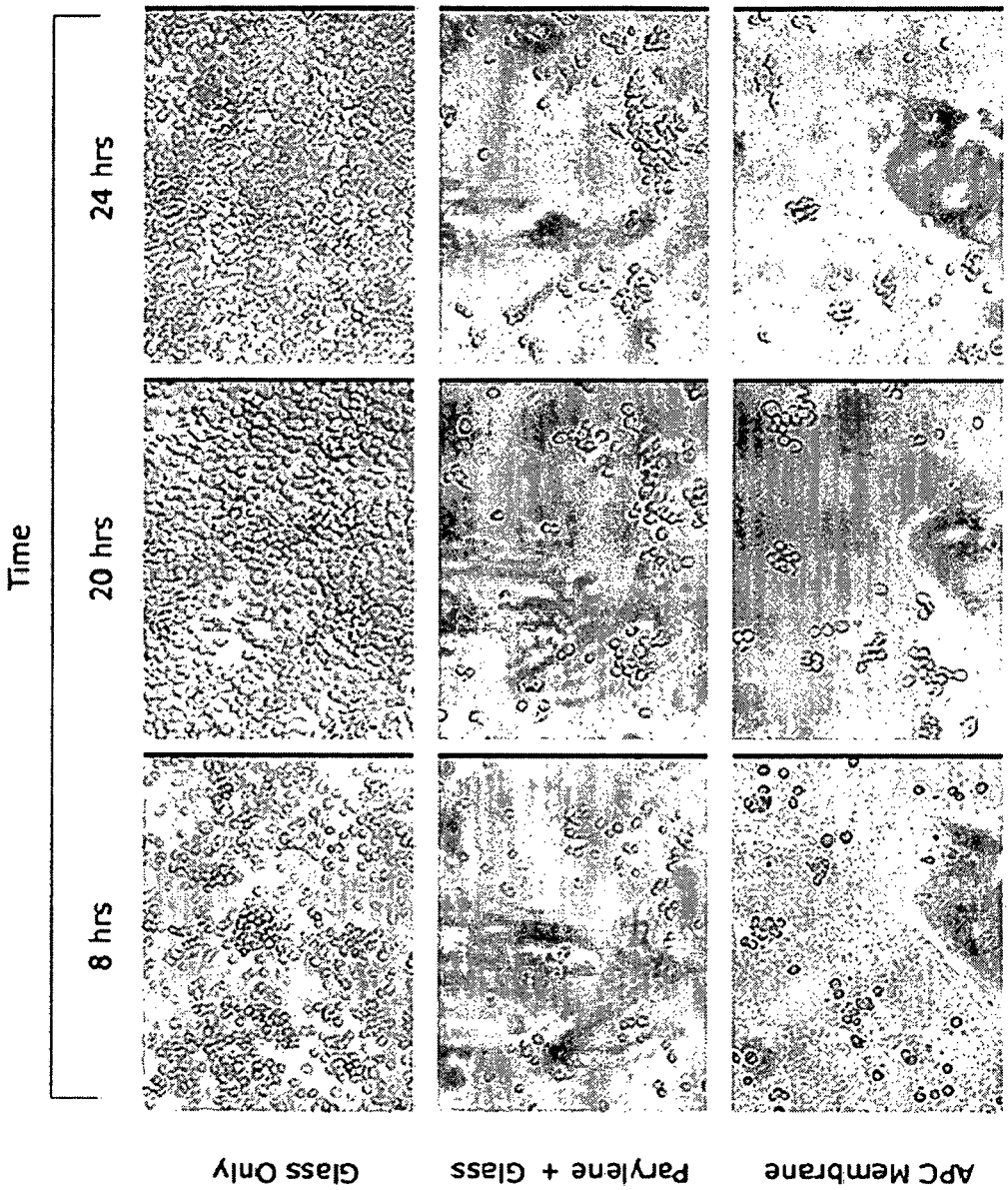
FIG. 14. Incubation of RAW 264.7 macrophages on glass, parylene, and APC membrane surfaces display differences in growth patterns. LPS stimulation occurred for 4 hours beginning after 20 hours of growth. Images were taken 8 hrs, 20 hrs, and 24 hrs. Qualitatively, cell growth was less confluent on the parylene and APC smfaces compared to glass. This observation suggests that growth and activity of macrophages are inhibited on the Parylene and APC surfaces. Closer inspection reveals that growth was almost completely halted on the APC membrane, while macrophages continued to grow on the parylene surface.

Following confirmation of Dex-copolymer composite film fabrication, Raw 264.7 were cultured atop the active substrates as well as bare glass slides and LPS was utilized to induce cellular stress and the production of a suite of inflammatory cytokines and signaling molecules (FIG. 4B, FIG. 10). LPS binds to the membrane-bound Toll-like receptor 4 (TLR4) that simulates bacterial infection and elicits the activation of transcriptional factors (e.g. Nuclear Factor kappa B (NFκB) for inflammatory cytokine production. For the purposes of this study, TNFα was selected as the cytokine marker for macrophage stress, and qPCR was utilized to examine the expression of TNFα mRNA (FIG. 5A). Macrophages activated by LPS that were cultured atop bare substrates resulted in significantly higher levels of inflammation over samples where LPS was introduced to macrophages that were cultured atop either 3 layers of Dex-copolymer composites. In addition, on samples where solutions of Dex were incubated directly with the glass culture slides/self-assembled without the polymer, LPS treatment of cultured macrophages resulted in the absence of inflammatory suppression that was previously observed with samples cultured atop the Dex/copolymer composites (data not shown).

Furthermore, studies were conducted to evaluate the effects of copolymer interaction upon cell growth to evaluate its potential application as a medically-relevant material such as an implant coating. Studies also examined the potential effects of solubilized polymer (e.g. polymer in solution) upon cellular growth and morphology. We incubated the polymer with the cell culture solutions (0.1 mg/ml-H₂O with sonication) to examine the impact of the polymer upon cell growth over multiple time points including 4 hrs, 24 hrs, and 48 hrs. These studies utilized a triblock copolymer which served as a larger structure to evaluate potential impact upon cellular growth. FIG. 5B shows that the cell growth and morphology were unaffected over the measured time period as the cells were able to undergo normal cell growth behavior. As such, this study showed that 1) Interfacially deposited Dex atop the polymeric amphiphiles could be dispensed to macrophages cultured atop the active composite, and 2) The copolymer is a biologically-amenable material that interacts favorably with cells in culture. As demonstrated by the qPCR trials, the copolymer served as both a buoying element at the air-water interface for the deposition of Dex, as well as a tethering component to maintain the integrity between the Dex and the glass substrate. This was an expected observation as the nature of the copolymer-substrate interaction, believed to be based upon a high density Van der Waals interaction, was previously demonstrated. As such, the intercalation of the Dex molecules within the strongly attached PEO-PMMA or PMOXA-PDMS-PMOXA copolymers was expected to be maintained, and potentially enhanced following endgroup crosslinking via UV exposure, a condition that may not be amenable towards more conventional, lipid-based amphiphiles that are less robust than the copolymer molecules. Suppression of LPS-mediated induction of TNFα in Raw 264.7 cells demonstrates the ability of our copolymers in suppressing immune response through Dex activation of glucocorticoid receptor, GR, which results in GR binding and inhibition NF-κB subunit, p65. The activation of GR by Dex has been previously shown to robustly inhibit NF-κB target genes through binding of p65 and blocking of p65 recruited transcriptional machinery, such as P-TEFb [22].

This study has demonstrated the concept of applying copolymer amphiphiles as the foundational element of fabricating thin films with versatile functionalities. Using both bioelectro-activity measurement and stress-suppression as exemplary cases, we have shown that the copolymer element enabled functional material (SWNT/Dex) deposition, and played a secondary role as an anti-protein adsorption and tethering component as well. As such, this methodology represents a broadly applicable technique for life science studies, drug delivery, as well as the fabrication of multifunctional electrodes for medical applications.

Example 7

Drug Dosing Based on Copolyer Layers

For the purposes of this study, TNFα was selected as the cytokine marker for macrophage stress, and RT-PCR was utilized to examine the expression of TNFα mRNA (FIG. 7). Macrophages activated by LPS that were cultured atop bare substrates resulted in significantly higher levels of inflammation over samples where LPS was introduced to macrophages that were cultured atop either 3, or 7 layers of Dex-copolymer composites. This outcome demonstrated that the drug-dosing capabilities of the hybrid material could be tailored based upon the number of layers deposited. Because the copolymer membrane dimensions are within the range of 2 nm (diblock)-4 nm (triblock) in thickness, coating substrates (e.g. implants) with multiple layers would result in minimal impact upon overall device dimensions. In addition, on samples where solutions of Dex were incubated directly with the glass culture slides/self-assembled without the polymer, LPS treatment of cultured macrophages resulted in the absence of inflammatory suppression that was previously observed with samples cultured atop the Dex/copolymer composites (FIG. 8). Self-assembled Dex without the copolymer substrate was unable to stay tethered to the glass slide for subsequent transfer to the macrophages (FIG. 9).

Example 8

APC Membrane Functionalized with Anti-Inflammatory Drug

In the initial studies the APC membranes the were functionalized with Dexamethasone (Dex), an anti-inflammatory drug. FIG. 11 provides a cross section view of the APC membrane. The base layer was comprised of a tangible layer of parylene that was deposited through vapor deposition with an SCS Coater. This resulted in an even layer of parylene free of pinholes to serve as the backbone of the APC membrane. In FIG. 11, the middle layer is the functionalized layer. In the present embodiment, the middle layer was functionalized with 300 uL of 5 mgl mL Dex. The Dex was incorporated via Langmuir-Blodgett deposition into a tri-block copolymer matrix, which secured the Dex molecules in a copolymer network matrix. Finally, another parylene layer was deposited to complete the membrane. The final parylene layer was an ultra-thin layer that had nanopores. FIG. 12 shows AFM images that were taken that suggest the possibility of nanopores on the surface of parylene. The darker areas indicate depressions on the surface that could be nanopores. As FIG. 12 shows, the surface of parylene is very rough terrain full of micro/nano-structures that potentially act as inflammatory stimuli. Comparing the AFM images of 0.03 g parylene with drug to 003g parylene without drug, it can be clearly seen that the layer of Dex incorporated into a copolymer matrix changes the terrain and is definitely present under the porous parylene layer. The same conclusion may be drawn from the comparison between the 0.05 g parylene with and without drug. FIG. 13 suggests that macrophages may be able to sense substrate stiffness and roughness to prompt an inflammatory response. The graph in FIG. 13A shows relative levels of iNOS expression between RAW 2643 murine macrophages cultured on parylene and parylene covered with a layer of copolymer. The bottom graph in FIG. 13B shows relative levels of TNF-a expression between RAW 264.7 murine macrophages grown on the different substrates. The graphs suggest that macrophages may sense the copolymer/parylene surface as a more biocompatible medium than parylene alone. However, the copolymer cannot be handled tangibly and parylene is needed as a backbone for the copolymer. The unique combination of copolymer and parylene is an integral and distinctive aspect of the APC membrane that simultaneously enables the copolymer to be handled, while taking advantage of its biomimetic properties and ability to be functionalized with an array of molecules.

Tissue culture images are shown in FIG. 14, which provides qualitative input on effects of growth on glass, parylene, and APC membrane substrates on cell development and morphology. The images of RAW 264.7 murine macrophage growth on glass, parylene, and APC membrane were taken over three time points. At 8 hours, the macrophages had been cultured in DMEM with 10% FBS and 1% Pen/Strep for 8 hours on their respective surfaces for the purpose of reaching the desired cell confluence on the various substrates; the plain glass slide served as the control. At the 8 hour time point, macrophage growth on the plain glass is about 60-70% confluent with minimal visible clumping. Contrasting growth on glass with growth on parylene and the APC membrane, it can be seen that the cell development is stunted; there is very little growth on the parylene and APC membrane substrates. This observation suggests that growth on parylene and the APC membrane is difficult for murine macrophages due to poor adhesion. This quality is very desirable and ideal for any implant and invasive biomedical device because cells are less likely to adhere to the device in problematic regions that could impair or even disable the function of the device. Images were taken again at 20 hours and immediately afterwards, 75 uL of 1 ug/mL lipopolysaccharide solution (LPS) was added to each sample to induce inflammation in the macrophages. At 20 hours before LPS induced inflammation, it can be seen that the cell growth is still virtually halted on the APC membrane and parylene surfaces; macrophages continue to multiply on plain glass reaching 90-95% confluence by 20 hours of growth.

LPS stimulation occurred for 4 hours and images were taken at the third time point (24 hours). In these images the macrophages growing on plain glass were well over 100% confluent. Growth on parylene increased slightly over these 4 hours with LPS stimulation, and there was no visible change in macrophage development on the APC membrane. These data warrant an observation made previously: a parylene or APC membrane layer on biomedical devices hinders macrophage adhesion due to inadequate traction on the aforementioned substrates. Diminished adhesion results in a more biomimetic material for invasive biomedical devices, but a suitable coating must also address the issue-of inflammation: the-APC membrane accomplishes this goal.

Figure 15:
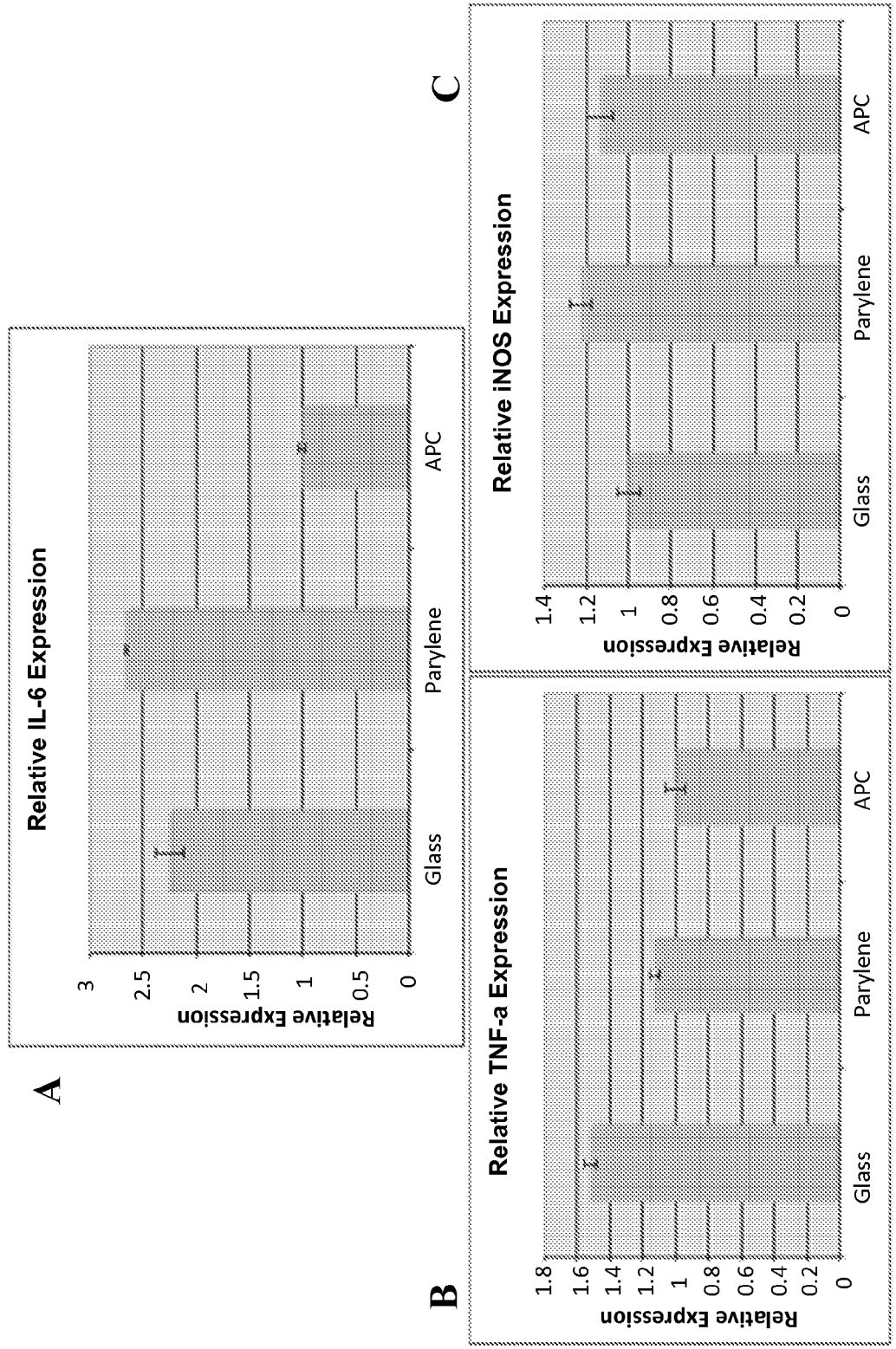
FIG. 15A. RT-PCR relative gene expression data for unsoaked slides confirm the presence of dexamethasone on the functionalized slides. Based on past studies, IL-6 expression values were most consistent and reliable possibly due to IL-6 occurring as a critical cytokinetic component for the immune response in murine macrophages. The expression of IL-6 is at least relatively two times higher for the parylene and glass slides compared to an APC membrane. This shows that Dex can successfully survive vapor deposition and soaking, and still be an effective inflammatory cytokine inhibitor.
FIG. 15B. The Same pattern is shown in relative TNF-a expression levels.
FIG. 15C. While this is not apparent in the relative iNOS expression levels, LPS induced inflammation may not have had a significant effect on iNOS levels. When taking the error bars into account, the levels of iNOS are comparable for the three surfaces.

FIG. 15 shows the data from RT-PCR gene expression studies done on the macrophages cultured on plain glass, parylene, and APC membrane. The macrophages were incubated on the substrates for 24 hours. After 20 hours, 75 uL of 1 ug/mL LPS was added to each sample to inflame the macrophages; LPS stimulation lasted for 4 hours. After 24 hours the macrophages were harvested. RNA isolation was achieved through cell lysis with Trizol reagent washes followed by chloroform extraction, centrifugation and isopropyl alcohol precipitation. cDNA was synthesized with 5× buffer, Oligo DT primer, reverse transctiptase, and the purified RNA samples. After a water bath at 37° C., the cDNA was mixed with primers for RT-PCR analysis. Three cytokines that control inflammation were investigated: TNF-a, IL-6 and iNOS (3-Actin was used to normalize the relative quantities of genes expressed). Relative IL-6 and TNF-a expression show an apparent decrease in secretion of IL-6 and TNF-a. The relative iNOS expression data did not show an advantage for any particular substrate. From past RT-PCR experiments conducted in the laboratory, iNOS was identified as an unpredictable cytokine; essentially, the results for iNOS were seldom consistent. FIG. 15C, when the error bars are taken into account iNOS expression levels are comparable across the different substrates. Additionally, past experiments have also determined IL-6 to be the most consistent inflammatory cytokine we have studied. The IL-6 data presented in FIG. 15A clearly show the APC membrane decreases inflammation up to 2.5 times compared to plain glass and parylene surfaces. The advantage that the functionalized drug-eluting, biocompatible APC membrane has over plain parylene was not apparent in our cell images, but RT-PCR shows inflammation is significantly reduced when macrophages are cultured on the APC membrane functionalized with Dex. Therefore, the APC membrane is a very biocompatible coating capable of eluting drug resulting in significantly reduced inflammation in RAW 2647 munine macrophages.

Figure 16:
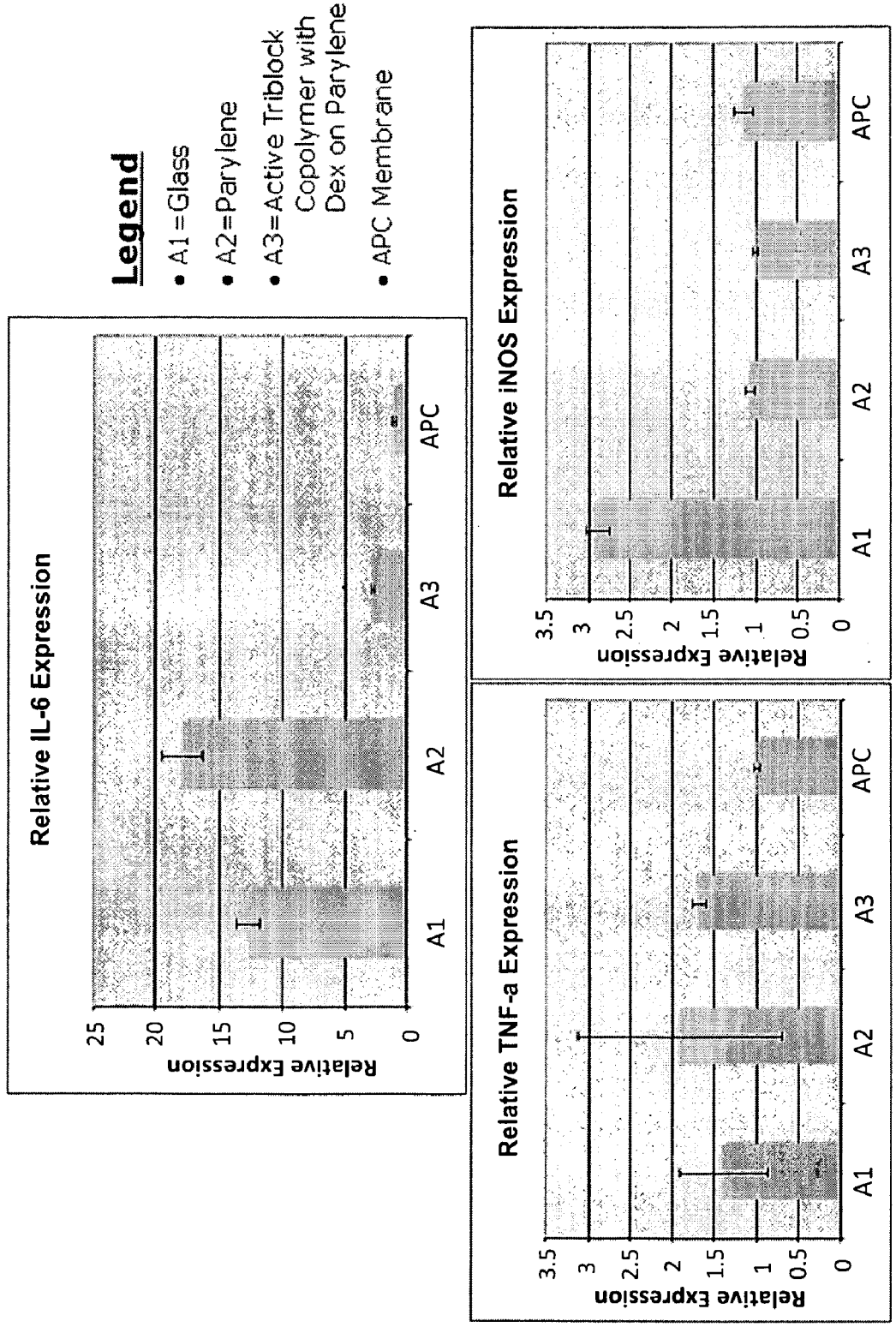
FIG. 16 RT-PCR relative gene expression data for soaked slides confirm the presence of dexamethasone on the functionalized APC membranes. Slide A3 is a functionalized slide with a parylene base and layers of Dex incorporated into a tri-block copolymer matrix, but lacks the final nanopore layer. The gene expression of IL-6 is higher for slide A3 compared to the APC membrane that has the nanopore layer engineered for slow elution capabilities. These data suggest that there is an advantage to slow elution owing to localization of drug elution to near the surface of the membrane. The APC membrane inhibits inflammatory cytokines, up to 18 times more effectively for IL-6 than does plain parylene on glass. The bare terrain of parylene was rough and littered with micro/nano-structured features that could serve as inflammatory stimuli.

FIG. 16 illustrates results of slow-elution studies through RT-PCR gene expression data. The samples represented in FIG. 16 were prepared differently from the samples in FIG. 15. To test slow-elution capabilities, the APC membrane was soaked in a Petri dish with DMEM (containing 10% FBS and 1% Pen/Strep) for 3 days prior to tissue culture. The plain glass and parylene samples were also soaked for 3 days to maintain uniformity in experimentation. After 3 days of soaking in media, macrophages were cultured on the samples. Soaking allowed the dexamethasone to elute slowly from the APC membrane. FIG. 16A shows relative IL-6 expression was 18 times less for the macrophages cultured on APC membrane than cells on parylene, and 13 times less than macrophages grown on plain glass.

These data suggest that a 3 day soak allowed the Dex to slowly diffuse through the nanopore layer, thus eluting more Dex into the media for interaction with macrophages. The samples presented in FIG. 15 were not soaked in media prior to tissue culture. Therefore, the macrophages harvested for FIG. 15 data were exposed to less drug because the Dex had less time to elute into the media. The effects of the difference between soaking and not soaking the membrane may be seen in relative gene expression graphs. The relative IL-6 expression of macrophages cultured on unsoaked membrane was over 2.5 times less than IL-6 expression of macrophages grown on parylene, but the soaked membrane resulted in over 18 times less IL-6 expression of macrophages grown on parylene. Therefore, RT-PCR data demonstrates that there was a clear advantage in soaking the membrane in in vitro studies, which translates to effective and prolonged bio-longevity of the biomedical device coated with APC membrane in a patient.

FIG. 16 also compares the APC membrane to a functionalized copolymer membrane with no nanopore layer engineered for slow elution. These data show that slow-elution is advantageous because it keeps the Dex that is eluted localized near the surface of the membrane where most of the effective dose can interact with macrophages to decrease inflammation. Even in a Petri dish, we can see the inefficiency of haphazard drug delivery; localized drug delivery through slow-elution is nearly 3 times more effective in reducing inflammation when compared to the functionalized copolymer membrane that elutes all the drug at once. This effect will be more pronounced in an actual patient where the strictly defined boundaries of a Petri dish are removed because the drug will have more area to diffuse through, which causes the effective dose to be diluted, and thus results in diminished treatment and drug efficacy.

In vitro studies indicate that the APC membrane is a versatile material capable of delivering Dex in a controlled fashion to maximize drug efficacy. Ultimately, the biocompatibility of the prylene and copolymer materials that was incorporated into the functionalized membrane, makes the APC membrane a low adhesion, biomimetic slow drugeluting tangible membrane and therefore, a prime candidate as an ideal biomedical device coating and platform for chemotherapeutics, anti-inflammatory treatments, and nanomedicine in the future.

Example 9

Industrial Applicability of the Embodiments

The APC membrane is a very versatile coating suitable for a broad scope of applications. The APC membrane has the potential to serve as a flexible drug delivery platform capable of diverse functionalization. Novel drugs are developed for countless therapeutics, but these drugs all need a method of delivery for their therapeutic potential to be realized. This method must be precise, biocompatible, and ideally, slow-eluting to prolong the time the drug may act in a patient; the APC membrane meets these requirements. Therefore, the APC membrane may be easily made into a drug-eluting patch for organs to deliver drugs to a specific part of the organ. An example of this application is a heart patch that could aid cardiac tissue regeneration by acting as a growth scaffold, for instance, after a heart attack by incorporating growth hormones into the copolymer matrix, the APC membrane may be used as a foundation for tissue regeneration and augmentation of cardiac, muscle, and vascular tissue among others.

In addition to serving as a drug conjugation and delivery platform, the APC membrane may also effectively coat implantable and invasive biomedical devices. The surface properties of the parylene surface may be "tuned" to enable effective switching of the parylene properties to either promote or resist cell adhesion depending on the specific application desired or implant being engineered. Such tuning can be employed to further enhance the versatility of the device as bio-interfacial properties are vital to the longevity of the device itself. Furthermore, when functionalized with Dex, the APC membrane significantly decreases inflammation and minimizes cell adhesion making it a biomimetic "skin" capable of boosting the biocompatibility and versatility of many biomedical devices, establishing the membrane as a relevant application for all future invasive medical technologies.

Example 10

In Vivo Characterization of Tri-Block Polymer Nanofilms

Figure 17:
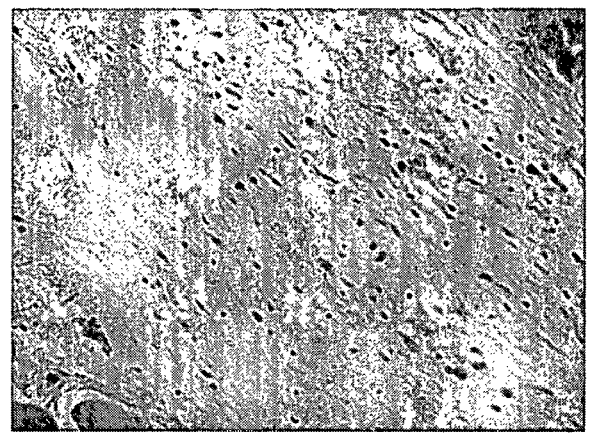
FIG. 17 shows histological analysis of Dex-copolymer nanofilm implantation as described in Example 10. Untreated tissue (17A), as well as tissue containing implanted uncoated disks (17B), as well as Dex-copolymer nanofilm coated disks (17C) were stained to examine cellular recruitment to the implant surface, which is a commonly observed mechanism of foreign body formation and eventual implant fouling.
Figure 17:
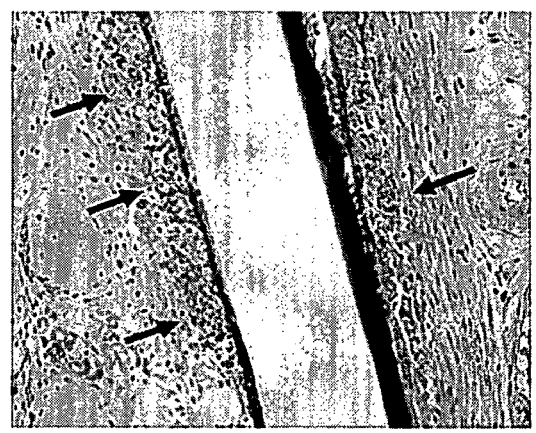
Figure 17:
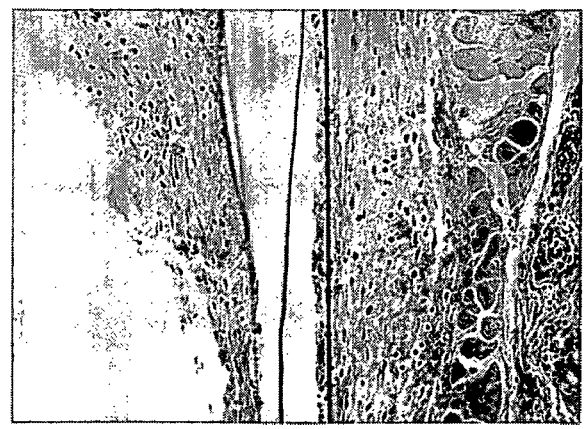

This Example describes in vivo studies that were carried out to examine the material-mediated blockage of cell aggregation around an implant site when nanofilm material is employed. Histological analysis was performed using Hematoxylin and Eosin (H&E) to image cell recruitment activity. Untreated tissue, tissue containing implanted uncoated disks, as well as Dex-copolymer nanofilms were stained to examine cellular recruitment to the implant surface which is a commonly observed mechanism of foreign body formation and eventual implant fouling (FIG. 17). C57b1/6 mice (n=6) were subcutaneously implanted dorsally with two polyethylene disks (Uncoated or PolyDex coated). Following 7 days, disks were excised, formalin fixed and Hematoxylin and Eosin stained. Samples were analyzed at 10× magnification. Representative images are presented. Black arrows indicate site of cell infiltration at the interface of the dermis and disk. FIG. 17A showed that the untreated tissue exhibits the presence of equally dispersed cells as shown by the nuclear stains. FIG. 17B showed that the implantation of disks only without nanofilm coatings exhibited a rapid recruitment of cells to the implant surface. Furthermore, FIG. 17C showed that the tissue that resided at the interface of the implant with the nanofilm showed the suppression of tissue inflammation. As such, the ability to translate the observed results from the in vitro study to in vivo applications was demonstrated using H&E analysis. The translational applicability of the material was further confirmed using F4/80 staining of the cells that were observed to aggregate around the implant site. This macrophage-specific stain showed that the cells that aggregated around the uncoated implant, and the cells that were precluded from aggregation around the polymer-coated implant were indeed macrophages.

Figure 18:
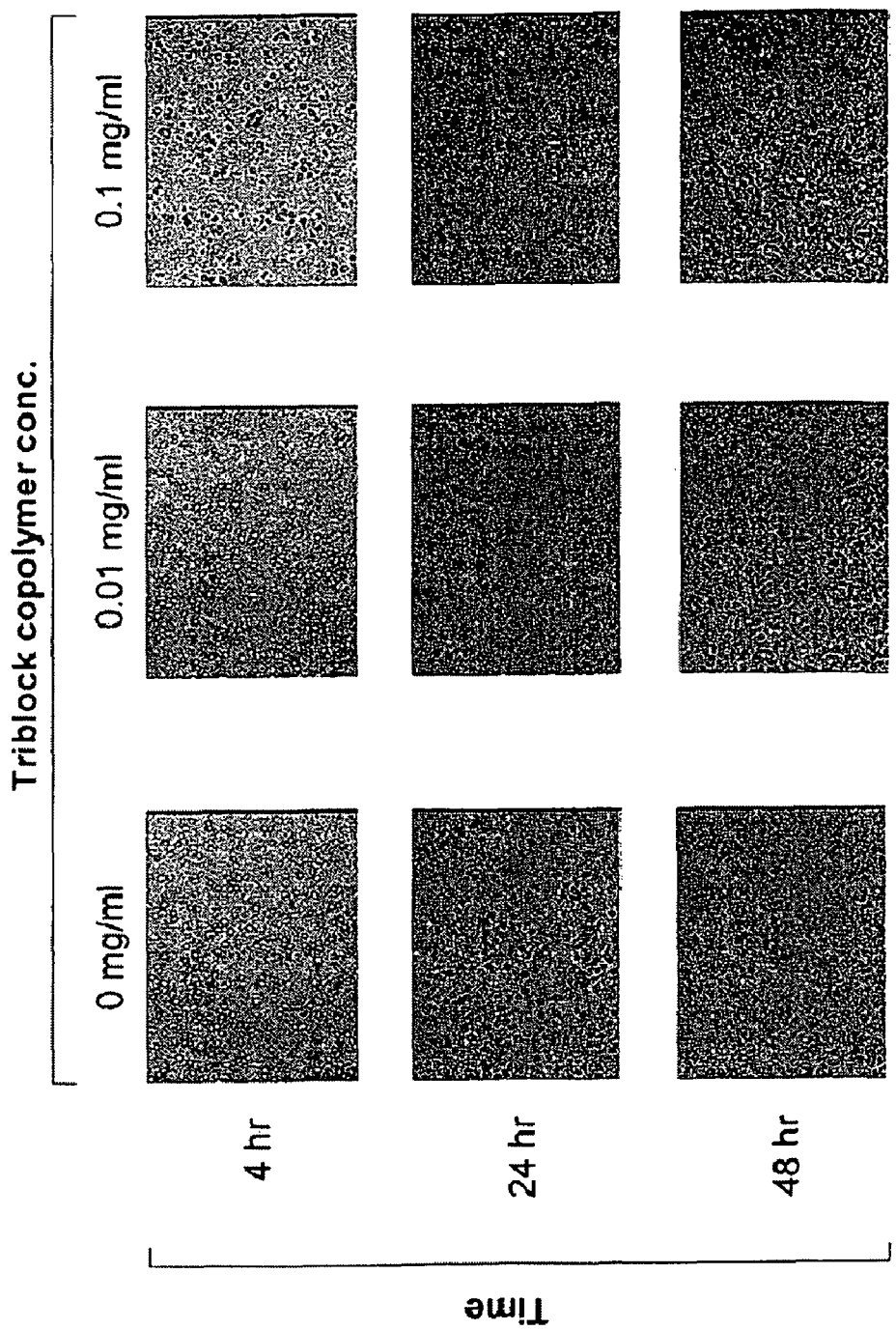
FIG. 18 shows that biologically inert polymer in solution has no effect upon cellular proliferation. Triblock copolymer in 0.01 mg/ml and 0.1 mg/ml concentrations were incubated with cultured macrophages. Samples were imaged using brightfield microscopy at 4 hrs, 24 hrs, and 48 hrs. Results show from in vitro standpoint that cellular proliferation is unaffected, confirming bio-inert properties of nanofilm.
Figure 19:
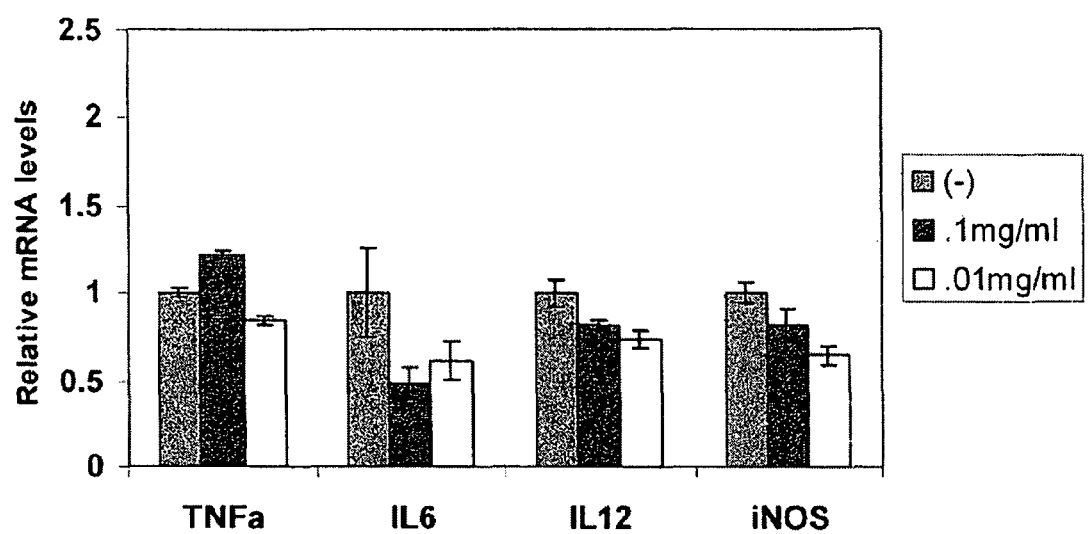
FIG. 19 shows that biologically inert polymer in solution has no effect upon cellular inflammatory gene programs. Triblock copolymer in 0.01 mg/ml and 0.1 mg/ml concentrations were incubated with cultured macrophages. Samples were lysed and RT-PCR was performed to examine the release of inflammatory cytokines/molecules. Results show negligible change compared with control readings (-) as changes exhibited changes of less than 2-fold.

Continued studies examined the potential effects of solubilized polymer (e.g. polymer in solution) upon cellular proliferation and normal cellular activity. Varying conventrations of the polymer were incubated with the cell culture solutions (0.01 mg/ml, 0.1 mg/ml) to examine the impact of the polymer upon cell growth over the multiple time points including 4 hrs, 24 hrs, and 48 hrs. FIG. 18 shows that the cell growth and morphology was unaffected which indicated that the polymer was indeed biologically-inert, further strengthening its application as an implant coating. The observed lack of adverse effects upon cell growth was further confirmed by examining the cellular inflammation programs of the macrophages exposed to the 0.01 mg/ml and 0.1 mg/ml polymeric concentrations (highest concentrations applied). FIG. 19 shows that the mRNA levels of TNFα, IL-6, IL-12, and iNOS are virtually unaffected, and actually decrease slightly when compared with the controls where no polymer was added, further confirming quantitatively that cellular activity is unaffected by the biologically-inert material. This Example has produced a comprehensive assessment of the potential that this nanopolymer-drug composite possesses as a robust and versatile implant coating that can provide localized cellular regulation using a variety of effector molecules situated on a spectrum of implant surfaces.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, it should be understood that changes and modifications can be made therein in accordance with ordinary skill in the art without departing from the invention in its broader aspects as defined in the following claims.

References

1. D. Ho, B. Chu, H. Lee, and C. D. Montemagno. 2004. Protein-driven energy transduction across polymeric biomembranes. Nanotechnology 15:1084-1094.

2. J. Xi, D. Ho, B. Chu, and C. D. Montemagno. 2005. Lessons Learned From Engineering Biologically-Active Hybrid Nano/Micro-devices. 2005 Advanced Functional Materials 15:1233-1240.

3. D. Ho, S. Chang, and C. D. Montemagno. 2006. Fabrication of biofunctional nanomaterials via *Escherichia coli* OmpF protein air-water interface insertion/integration with copolymeric amphiphiles. Nanomedicine 2:103-112.

4. A. Graff, M. Sauer, P. van Gelder, and W. Meier. 2002. Virus-Assisted Loading of Polymeric Nanocontainers. Proc. Nat. Acad. Sci. 99:5064-5068.

5. C. Nardin, T. Hirt, J. Leukel and W. Meier. 2000. Polymerized ABA-triblock copolymer vesicles. Langmuir 16:1035-1041.

6. D. Ho, B. Chu, H. Lee, E. K. Brooks, K. Kuo, and C. D. Montemagno. 2005. Fabrication of biomolecule-copolymer hybrid nanovesicles as energy conversion systems. Nanotechnology. 16:3120-3132.

7. H. Lee, D. Ho, and C. D. Montemagno. 2006. Fluorometric Measurement of Vectorially-Inserted Purple Membrane Activity Across Block Copolymer Thin Films. Polymer 47:2935-2941.

8. W. Stoeckenius, R. H. Lozier, and R. A. Bogomolni. 1979. Structure of biological membranes. Biochem. Biophys. Acta 505:215-278.

9. J. F. Rathman, and P. Sun. 2005. Biocomposite films synthesized at a fluid/fluid interface. Faraday Disc. 129:193-203.

10. G. Grant, D. Koktysh, B. Yun, R. Matts, and N. Kotov. 2001. Layer-By-Layer Assembly of Collagen Thin Films: Controlled Thickness and Biocompatibility. Biomed. Microdev. 3:301-306.

11. M. M. Ghannam, M. M. Mady, and W. Khalil. 1999. Interaction of type-I collagen with phospholipid monolayer. Biophys. Chem. 80:31-40.

12. W. Meier, C. Nardin, and M. Winterhalter. 2000. Reconstitution of Channel Proteins in (Polymerized) ABA Triblock Copolymer Membranes. Angew. Chim. Int. Ed. 39:4599-4602.

13. C. Nardin, M. Winterhalter, W. Meier. 2000. Giant Free-Standing ABA Triblock Copolymer Membranes. Langmuir. 16:7708-7712.

14. D. Ho, B. Chu, J. J. Schmidt, E. Brooks, and C. D. Montemagno. 2004. Hybrid Protein/Polymer Biomimetic Membranes. IEEE Trans. Nanotechnology. 3:256-263.

15. Lee, H., D. Ho, J. J. Schmidt, and C. D. Montemagno. 2003. Biosolar Powered Fabric. IEEE Proceedings on Nanotechnology 2:733-736.

16. D. Ho, B. Chu, K. Kuo, and C. D. Montemagno. 2004. Functionalizing Biomimetic Membranes with Energy Transducing Proteins. Proc. of the Mat. Res. Soc. 823:W11.8.1-W11.8.6.

17. S. Applequist, R. P. A. Wallin, and H. G. Ljunggren. 2002. Variable expression of toll-like receptor in murine innate and adaptive immune cell lines. International Immunity 9:1065-1074.

18. A. K. Perry, E. K. Chow, J. B. Goodnough, W. C. Yeh, and G. Cheng. 2004. Differential requirement for TANK-binding kinase-1 in type I interferon responses to toll-like receptor activation and viral infection. The Journal of experimental medicine. 199:1651-1658.

19. S. E. Doyle, R. O'Connell, S. A. Vaidya, E. K. Chow, K. Yee, and G. Cheng. 2003. Toll-like receptor 3 mediates a more potent antiviral response than Toll-like receptor 4. Journal of immunology 170:3565-3571.

20. S. Terrettaz, J. Chen, C. J. Miller, and R. D. Guiles. 1996. Kinetic Parameters for Cytochrome c via Insulated Electrode Voltammetry. Journal of the American Chemical Society. 118:7857-7858.

21. A. Szucs, and M. Novak. 1995. Stable and Reversible Electrochemistry of Cytochrome-C on Bare Electrodes .2. Effects of Experimental Conditions. Journal of Electroanalytical Chemistry, 383:75-84.

22. H. F. Luecke and K. R. Yamamoto. 2005. The glucocorticoid receptor blocks P-TEFb recruitment by NFkappaB to effect promoter-specific transcriptional repression. Genes Dev. 19:1116-1127.

1B. E. Grube et al, "Six-month clinical and angiograplric results of a dedicated drug-eluting stent for the treatment of coronary bifurcation narrowings," The American Journal of Cardiology, vol 99, pp 1691-1697,2007.

2B. M Sokolsky-Papkov, K. Agaslri, A, Glaye, K. Shakesheff, A J Domb, "Polymer carriers for drug delivery in tissue engineering," Advanced Drug Delivery Reviews, voL 59, pp 187-206,2007.

3B. H M Butt W. L Hunter, "Thug-eluting stents: A multidisciplinary success Story," Advanced Drug Delivery Reviews, vol. 58, pp 350-357,2006.

4B H M Butt, W L. Hunter, "Drug-eluting stents: an innovative multidisciplinary drug delivery platform," Advanced Drug Delivery Reviews, vol 58, pp. 345-0346, 2006.

5B. M. M. Kirucoff, A Bomn, D G. Schultz, "Drug-eluting stents 'deliver heartburn'—How do we spell relief going forward," Circulation, vol 115, pp. 2990-2994, 2007.

6B. D. Ho, R Chu, H Lee, and C. D. Montemagno. 2004 Protein-driven energy transduction across polymeric biomembranes Nanotechnology 15:1084-1094.

7B J. Xi, n. Ho, B Chu, and C. D Montemagno 2005. Lessons Learned From Engineering Biologically-Active Hybrid NanolMicro-devices. 2005 Advanced Functional Materials 15:1233-1240.

8B. D Ho, S. Chang, and CD. Montemagno. 2006. Fabrication of biofunctional nanomaterials via *Escherichia coli* OmpF protein air water interface insertion/integration with copolymeric amphiphiles Nanomedicine 2: 103-112.

9B. A Graff, M Sauer, P van Gelder, and W Meier. 2002 Virus-Assisted Loading of Polymeric Nanocontainers. Proc Nat. Acad. Sci. 99:5064-5068.

10B. C Nardin, I. Hirt, 1 Leukel and W. Meier 2000 Polymerized ABA-tri-block copolymer vesicles. Langmuir 16:1035-1041.

11B. D. Ho, B Chu, H Lee, E. K. Brooks, K. Kuo, and C D Montemagno. 2005 Fabrication of biomolecule-copolymer hybrid nanovesicles as energy conversion systems. Nanotechnology 16:31203132.

12B H. Lee, D. Ho, and CD. Montemagno. 2006 Fluorometric Measurement of Vectorially Inserted Purple Membrane Activity Across Block Copolymer Thin Films Polymer 47:2935-2941.

13B W Stoeckenius, R H Lozier, and R. A Bogomolni. 1979. Structure of biological membranes, Biochem. Biophys Acta 505:215-278.

14B J F Rathman, and P. Sun 2005. Biocomposite films synthesized at a fluid/fluid interface, Faraday Disc 129: 193-203.

15B G Grant, D. Koktysh, B Yun, R Matts, and N Kotov 2001 Layer-By-Layer Assembly of Collagen Thin Films: Controlled Thickness and Biocompatibility Biomed Microde v 3:301•306.

16B M. M Ghannam, M. M. Mady, and W Khalil 1999 Interaction of type-1 collagen with phospholipid monolayer, Biophys. Chem. 80:31-40.

17B W. Meier, C Nardin, and M. Winterhalter. 2000 Reconstitution of Channel Proteins in (polymerized) ABA Tri-block Copolymer Membranes. Angew Chim Int Ed 39:4599-4602.

18B. C Nardin, M Winterhalter, W Meier 2000. Giant Free-Standing ABA Tri-block Copolymer Membranes Langmuir. 16:7708-7712.

19B P. B Malafaya, G A, Silva, R. L Reis, "Natural-origin polymers as carriers and scaffolds for biomolecules and cell delivery in tissue engineering application," Advanced Drug Delivery Reviews, vol 59, pp 207-233,2007.

20B. N Stark, "Literature review: Biological safety of parylene C," Medical Plastics and Biomaterials, p. 30, March 1996

21B. L. Wolgemuth, "Assessing the performance and suitability of parylene coating," Medical Device and Diagnostic Industry, p 42, August 2000.

22B. H. L, Wong et aL, "Chemotherapy with anticancer drugs encapsulated in solid lipid nanoparticles," Advanced Drug Delivery Reviews, 2007.

23B. D. W, Grattan and M, Bilz, "The thermal aging of parylene and the effect of antioxidant," Studies in Conservation, voL 36, pp 44-52, 1991.

24B. D Ho, R Chu, J J Schmidt, E Brooks, and CD Montemagno. 2004 Hybrid Protein Polymer Biomimetic Membranes IEEE Trans. Nanotechnology 3:256-263

25B. Lee, H, D Ho, J J Schmidt, and C D. Montemagno 2003 Biosolar Powered Fabric IEEE, Proceedings on Nanotechnology 2:733-736.

26B. D. Ho, B. Chu, K Kuo, and CD. Montemagno 2004 Functionalizing Biomimetic Membrane with Energy Transducing Proteins. Proc. of the Mat Res. Soc 823:W1181-W118.6.

27B. S Applequist, R P A Wallin, and H. G. Ljunggren. 2002 Variable expression of toll-like receptor in murine innate and adaptive immune cell lines. International Immunity 9:1065-1074.

28B. A K Perry, E K Chow, I B Goodnough, W. C Yeh, and G. Cheng 2004. Differential requirement for TANK-binding kinase-I in type I interferon responses to toll-like receptor activation and vital infection. The journal of experimental medicine 199:1651-1658.

29B S. E. Doyle, R O'Connell, S. A Vaidya, E. K Chow, K Yee, and G Cheng 2003 Toll-like receptor 3 mediates a more potent antiviral response than Toll-like receptor 4. Journal of immunology, 170:3565-3571.

30B S. Terrettaz, I Chen, C L Miller, and R. D. Guiles. 1996. Kinetic Parameters for Cytochromec via Insulated Electrode Voltammetry Journal of the American Chemical Society 118:7857-7858.

31B A Szucs, and M Novak 1995 Stable and Reversible Electrochemistry of Cytochrome-C on Bare Electrodes Effects of Experimental Conditions. Journal of Electoanalytical Chemistry, 383:7584.

32B. H. F. Luecke and K R. Yamamoto 2005. The glucocorticoid receptor blocks P-TEFb recruitment by NFkappaB to effect promoter-specific transcriptional repression Genes Dev 19:11161127.

We claim:

1. An implantable medical device having one or more of its surfaces coated with a nanofilm composition comprising:
   (a) a first layer comprising parylene;
   (b) a second layer comprising a copolymer; and
   (c) a third layer comprising nanoporous parylene,
   wherein the copolymer is a triblock copolymer comprising polymethyloxazoline-polydimethylsiloxane-polymethyloxazoline, and wherein the nanofilm has a thickness between 0.1 nm and 20 nm.

2. The device of claim 1, wherein said composition further comprises at least one therapeutic agent.

3. The device of claim 2, wherein the at least one therapeutic agent is not a protein.

4. The device of claim 2, wherein the at least one therapeutic agent is selected from the group consisting of: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents.

5. The device of claim 1, wherein the copolymer comprises a single layer having a thickness from about 1 nm to about 10 nm.

6. The device of claim 1, wherein the device comprises an electrode.

* * * * *